U S011278219B2

United States Patent
Gassler et al.

(10) Patent No.: US 11,278,219 B2
(45) Date of Patent: Mar. 22, 2022

(54) FLUID HANDLING DETECTORS

(71) Applicant: W. L. Gore & Associates, Inc., Newark, DE (US)

(72) Inventors: Paul D. Gassler, Newark, DE (US); Austin J. Crouse, Newark, DE (US); Sean R. Coyer, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 16/651,191

(22) PCT Filed: Sep. 28, 2018

(86) PCT No.: PCT/US2018/053643
§ 371 (c)(1),
(2) Date: Mar. 26, 2020

(87) PCT Pub. No.: WO2019/068047
PCT Pub. Date: Apr. 4, 2019

(65) Prior Publication Data
US 2020/0268293 A1    Aug. 27, 2020

Related U.S. Application Data

(60) Provisional application No. 62/565,746, filed on Sep. 29, 2017.

(51) Int. Cl.
*A61B 5/145* (2006.01)
*A61B 5/00* (2006.01)

(52) U.S. Cl.
CPC ...... *A61B 5/14546* (2013.01); *A61B 5/14517* (2013.01); *A61B 5/6801* (2013.01); *A61B 2560/0462* (2013.01); *A61B 2562/164* (2013.01)

(58) Field of Classification Search
CPC . A61B 5/145; A61B 5/14517; A61B 5/14546; A61B 5/14532; A61B 5/6801; A61B 5/1477; A61B 5/6833
See application file for complete search history.

(56) References Cited

U.S. PATENT DOCUMENTS 5,076,273 A * 12/1991 Schoendorfer .... A61B 5/14521
600/573
6,063,029 A     5/2000 Saita et al.

FOREIGN PATENT DOCUMENTS

| WO | WO-8702267 A1 * | 4/1987 | ......... G01N 33/5002 |
| WO | WO-2009025698 A1 * | 2/2009 | ........... A61B 5/4881 |
| WO | WO-2011008581 A2 * | 1/2011 | ............ G01N 33/52 |
| WO | WO-2015184065 A1 * | 12/2015 | ......... A61B 5/14517 |
| WO | WO-2015184072 A1 * | 12/2015 | ........... A61B 5/0531 |

(Continued)

OTHER PUBLICATIONS

"GORE Microfiltration Media" datasheet (Year: 2021).*
(Continued)

*Primary Examiner* — Eric F Winakur
*Assistant Examiner* — Alice Ling Zou

(57) ABSTRACT

Devices for collecting and analyzing a fluid sample comprise a fluid-collecting porous material comprising at least one hydrophilic porous layer and one or more sensors adapted to provide a response to the presence of an analyte. The detectors are useful for collecting and analyzing a very small volume of sample and may include features that facilitate and direct flow of the sample through porous material.

19 Claims, 15 Drawing Sheets

(56) References Cited

FOREIGN PATENT DOCUMENTS

| WO | WO-2016134235 A1 * | 8/2016 | ......... A61B 5/14517 |
|----|---|---|---|
| WO | 2017/019573 A1 | 2/2017 | |
| WO | WO-2017070640 A1 * | 4/2017 | ......... A61B 5/14546 |
| WO | 2017/075402 A1 | 5/2017 | |

OTHER PUBLICATIONS

"Bubble Point Integrity Test," Scott Laboratories, https://scottlab.com/bubble-point (Year: 2021).*
International Search Report and Written Opinion from International Application No. PCT/US2018/053643 dated Jan. 24, 2019.
"Bubble Point", Wikipedia, Retrieved on Jan. 17, 2019 «https://en.wikipedia.org/wiki/Bubble_point».

* cited by examiner

FLUID HANDLING DETECTORS

CROSS-REFERENCE

The present application is a national phase filing under 35 USC 371 of International Application No. PCT/US2018/053643, filed on Sep. 28, 2018, claiming priority to U.S. Provisional Patent Application No. 62/565,746, filed Sep. 29, 2017, the entire contents and disclosures of which are incorporated herein in their entirety.

FIELD

The present disclosure relates generally to the field of detectors for bodily fluids, and in particular to the fluid handling of those bodily fluids in those detectors.

BACKGROUND

In healthcare there is a need for continuous, non-invasive monitoring of physiological analytes, i.e. biomarkers, for assessing human performance, health and wellbeing. Although these analytes are present in blood, obtaining a blood sample requires an invasive sample collection, so other analyte sources may be preferred.

Widely recognized as being easily accessible, sweat and interstitial fluid can provide important information. Sweat contains many of the analytes that are carried in other bodily fluids, such as blood, which can provide significant information which enables one to diagnose ailments, health status, toxins, performance, and other physiological attributes even in advance of any physical sign. Furthermore, sweat itself, and the action of sweating, or other parameters, attributes, solutes, or features on or near skin or beneath the skin, can be measured to further reveal physiological information. Thus, sweat sensing technologies can be used with wide ranging applications from athletics, to first-responders and military, to pediatrics, to pharmacological monitoring, to personal digital health. The sensors can measure one analyte, such as sodium, chloride, or potassium ions, or combinations of analytes. One application would allow diabetics to monitor blood glucose without drawing blood. Another application is early detection of toxins in at-risk individuals, and, in particular, children.

Although humans have millions of sweat glands, collecting a sufficient volume of sweat is challenging. Sweat is difficult to collect for analysis either because of a lack of production, evaporation, or collection errors. Also collecting fresh sweat and replacing older sweat can cause problems for sensing applications. Accumulation of older sweat can lead to inaccurate readings.

Thus, there remains a need for improved fluid handling to collect a sample containing analytes for sensing applications. The properties and advantages of the present invention will become apparent to those of skill in the art upon reading the following disclosure.

SUMMARY

Covered embodiments are defined by the claims, not this summary. This summary is a high-level overview of various aspects and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

In some embodiments, a detector detecting an analyte in a sample as described herein includes a fluid-collecting porous material including a sample-collection surface and an analyte detection surface, the fluid-collecting porous material including at least one hydrophilic porous layer; and one or more sensors mounted to the analyte-detection surface. In some embodiments, the hydrophilic porous layer includes hydrophilic regions and hydrophobic regions, wherein the hydrophilic regions form a first hydrophilic surface area on the sample-collection surface and a second hydrophilic surface area on the analyte-detection surface, and wherein the first hydrophilic surface area is greater than the second hydrophilic surface area. For example, the hydrophilic porous layer optionally may include hydrophilic regions and hydrophobic regions, wherein the hydrophilic regions and hydrophobic regions form microfluidic hydrophilic channels between the sample-collection surface and the analyte-detection surface. In some embodiments, the at least one hydrophilic porous layer includes a fluoropolymer, polyurethane, polyolefin, polyester, polymeric organosilicon compound, or a combination thereof.

The fluid-collecting porous material optionally may include at least two adjacent hydrophilic layers, wherein a first hydrophilic layer includes the sample-collection surface and a second hydrophilic layer includes the analyte-detection surface, and wherein the first and second hydrophilic layers are arranged with the sample-collection surface in fluid communication with the analyte-detection surface. In some embodiments, the first hydrophilic porous layer has a larger pore size than the second hydrophilic porous layer. In some embodiments, the first hydrophilic porous layer is conformable to a surface upon which the sample is collected. In some embodiments, the second hydrophilic porous layer has a mass to area ratio of 4 grams per square meter (gsm) or less and/or has a bubble point of greater than 65 kPa. The second hydrophilic porous layer optionally may displace the sample laterally in the portion covered by the one or more sensor. For example, the area of the displaced sample optionally may be at least 20 $mm^2$ in the second hydrophilic porous layer.

The sample collecting surface optionally may include pores having a size small enough to filter 97% of particulates having a diameter of greater than 0.07 microns from the sample. The sample-collection surface and analyte-detection surface optionally may each include a material not dissolvable in water. The detector optionally may further include a liquid-proof barrier layer covering the one or more sensors and a portion of the analyte-detection surface, the liquid proof barrier including a polymeric material or resin. In some embodiments, the analyte-detection surface includes an exposed surface region adjacent to and outside of the liquid-proof barrier layer.

In some embodiments, a detector detecting an analyte in a sample as described herein includes a hydrophilic porous layer having a mass to area ratio of 4 gsm or less and a first surface opposite a second surface; and one or more sensors mounted to the second surface, wherein the one or more sensors are adapted to provide a response to the presence of an analyte in sample. For example, the mass to area ratio of the hydrophilic porous layer is 3 gsm or less or optionally may be from 0.5 to 4 gsm. In some embodiments, the at least one hydrophilic porous layer includes a fluoropolymer, polyurethane, polyolefin, polyester, polymeric organosilicon compound, or a combination thereof. In some embodiments, the hydrophilic porous layer has a bubble point of greater than 65 kPa. In some embodiments, the hydrophilic porous layer displaces the sample laterally in the portion covered by the one or more sensor. The detector optionally may further include a second hydrophilic layer including a sample-collection surface, wherein the second hydrophilic layer is adjacent to the first surface. In some embodiments, the second hydrophilic layer has a larger pore size than the first hydrophilic porous layer.

In some embodiments, a detector detecting an analyte in a sample as described herein includes a porous material including a first hydrophilic porous layer and an adjacent second hydrophilic layer, wherein the first hydrophilic layer includes a sample-collection surface and the second hydrophilic layer includes an analyte-detection surface, and wherein the first hydrophilic layer includes a bubble point at least 50 kPa lower than a bubble point of the second hydrophilic layer; and one or more sensors mounted to the analyte detection surface, wherein the one or more sensors are adapted to provide a response to the presence of an analyte in sample. For example, the bubble point of the first hydrophilic layer optionally may be at least 60 kPa lower than a bubble point of the second hydrophilic layer or optionally may be at least 70 kPa lower than a bubble point of the second hydrophilic layer. In some embodiments, the second hydrophilic porous layer has a bubble point of greater than 65 kPa, greater than 100 kPa, greater than 150 kPa, or greater than 175 kPa.

The first and/or the second hydrophilic porous layer optionally may include a fluoropolymer, polyurethane, polyolefin, polyester, polymeric organosilicon compound, or a combination thereof. The second hydrophilic porous layer optionally may displace the sample laterally in the portion covered by the one or more sensor.

In some embodiments, a detector detecting an analyte in a sample as described herein includes at least one hydrophilic porous layer having a thickness from 0.5 to 50 μm, and a first surface opposite a second surface; and one or more sensors mounted to the second surface, wherein the one or more sensors are adapted to provide a response to the presence of an analyte in sample. For example, the thickness of the at least one hydrophilic porous layer optionally may be from 1 to 5 μm. The at least one hydrophilic porous layer optionally may have a bubble point of greater than 65 kPa.

The at least one hydrophilic porous layer optionally may include a fluoropolymer, polyurethane, polyolefin, polyester, polymeric organosilicon compound, or a combination thereof. The second hydrophilic porous layer optionally may displace the sample laterally in the portion covered by the one or more sensor. The detector optionally may further include a second hydrophilic layer including a sample-collection surface, wherein the second hydrophilic layer is adjacent to the first surface. In some embodiments, the second hydrophilic layer has a larger pore size than the first hydrophilic porous layer. The second hydrophilic layer optionally may include a larger pore size than the hydrophilic porous layer. The second hydrophilic layer optionally may include an average thickness from 5 pm to 100 pm. The second hydrophilic layer optionally may include a non-uniform thickness.

In some embodiments, a detector detecting an analyte in a sample as described herein includes a hydrophilic porous layer having a mass to area ratio of 4 gsm or less, a bubble point of at least 65 kPa, and a thickness from 0.5 to 50 μm, and a first surface opposite a second surface; and one or more sensors mounted to the second surface, wherein the one or more sensors are adapted to provide a response to the presence of an analyte in sample.

In some embodiments, a detector detecting an analyte in a sample as described herein includes a porous material including a reservoir layer having a hydrophilic region and a hydrophobic region, and a collection layer including a collecting surface opposite the reservoir layer, wherein the collecting surface is in fluid communication with the reservoir layer; and one or more sensors mounted to the hydrophilic region, wherein the one or more sensors are adapted to provide a response to the presence of the analyte. In some embodiments, the collection layer includes at least one hydrophilic region. In some embodiments, the reservoir layer has a mass to area ratio of 4 gsm or less and/or a bubble point of 65 kPa or more and/or a thickness from 0.5 to 50 μm.

The porous material optionally may include a fluoropolymer, polyurethane, polyolefin, polyester, polymeric organosilicon compound, or a combination thereof. The hydrophilic region of the reservoir layer optionally may include a coated expanded polytetrafluoroethylene. In some embodiments, the hydrophilic region of the reservoir layer has a larger pore size than the collection layer. The collection layer optionally may be conformable to a surface upon which the sample is collected. The collection layer optionally may include pores having a size small enough to filter 97% of particulates having a diameter of greater than 0.07 microns from the sample. In some embodiments, the detector further includes a liquid-proof barrier layer covering the one or more sensors and a portion of the reservoir layer, the liquid proof barrier including a polymeric material or resin.

In some embodiments, a detector detecting an analyte in a sample as described herein includes hydrophilic layer having a first surface including a hydrophobic region and a hydrophilic region, and a second surface including a hydrophobic region and a liquid-barrier region; and one or more sensors mounted within the hydrophilic layer on the hydrophobic region of the first surface, wherein the one or more sensors are adapted to provide a response to the presence of the analyte.

In some embodiments, a detector detecting an analyte in a sample as described herein includes a porous material having a hydrophilic region surrounded by a hydrophobic region, wherein the hydrophilic region includes a collection zone, a pathway and an evaporation zone, wherein the pathway provides a fluid connection between the collection zone and evaporation zone; one or more sensors mounted to the pathway; and a liquid-proof barrier layer covering the one or more sensors, pathway and collection zone. In some embodiments, the one or more sensors are adapted to provide a response to the presence of the analyte flowing through the pathway from the collection zone to the evaporation zone. In some embodiments, the hydrophobic region partially surrounds the hydrophilic region. The porous material optionally may include a fluoropolymer, polyurethane, polyolefin, polyester, polymeric organosilicon compound, or a combination thereof. The hydrophilic region of the porous material optionally may include a coated expanded polytetrafluoroethylene. In some embodiments, the hydrophilic region of the porous material has a mass to area ratio of 4 gsm or less and/or a thickness from 0.5 to 50 μm and/or a bubble point of greater than 65 kPa. In some embodiments, the porous material is a second porous layer and the detector further includes a first porous layer opposite the liquid-proof barrier layer, wherein the first porous layer includes a bubble point at least 50 kPa lower than a bubble point of the second porous layer.

In any embodiment described herein, the one or more sensors optionally may be adapted to provide a response to the presence of an analyte in sample. In an embodiment described herein, the analyte optionally may be a protein, cytokine, ion, metabolite, glucose, glucose oxidase, enzyme, hormone, DNA, peptide or combinations thereof. In any embodiment described herein, the one or more sensors optionally may be adapted to provide a response to a pH, temperature, humidity, or impedance. In any embodiment described herein, the sample optionally may be sweat, blood, urine, salvia, interstitial fluid, or other bodily fluid.

In any embodiment described herein, the detector optionally may further include an adhesive for adhering the detector and/or optionally may further including a stimulator for heating the sample. In any embodiment described herein, the sample optionally may be collected directly into the detector without passing through a volume of oil. In any embodiment described herein, the sensor optionally may be in the pores of the hydrophilic region. In any embodiment described herein, the flow of the sample optionally may be 0.1 to 5 nL per minute per gland. In any embodiment described herein, the sensor optionally may be porous.

In some embodiments, a detector for detecting an analyte in a sample collected on skin of a subject includes a first layer having a first side and a second side opposite the first side, wherein the first layer comprises a synthetic porous membrane having a first average pore size, wherein at least a portion of the first layer is hydrophilic, and wherein the first layer is configured to conform to the skin; a second layer having a first side and a second side opposite the first side, wherein the second layer is coupled to the first layer such that at least a portion of the first side of the second layer is directly adjacent to at least a portion of the second side of the first layer, and wherein the second layer comprises a synthetic porous membrane having a second average pore size that is smaller than the first average pore size, wherein at least a portion of the second layer is hydrophilic; and at least one sensor configured to detect the analyte, wherein the at least one sensor is mounted to at least one of (a) the first layer, or (b) the second layer.

In some embodiments, the at least one sensor is mounted to the second side of the second layer.

In some embodiments, the detector also includes a liquid-proof layer overlaying at least a portion of the second side of the second layer so as to cover the at least one sensor.

In some embodiments, the second layer includes a hydrophilic region and a hydrophobic region. In some embodiments, the at least one sensor is mounted to the second side of the second layer so as to be positioned on the hydrophilic region of the second layer. In some embodiments, the hydrophobic region of the second layer includes a barrier.

In some embodiments, the first layer includes a hydrophilic region and a hydrophobic region. In some embodiments, the hydrophilic region of the first layer is offset from the hydrophilic region of the second layer. In some embodiments, the hydrophobic region of the first layer includes a barrier positioned on the first side of the first layer. In some embodiments, the at least one sensor is positioned between the barrier and the hydrophobic portion of the first layer.

In some embodiments, the at least one sensor is positioned between the hydrophilic region of the first layer and the hydrophilic region of the second layer.

In some embodiments, the hydrophobic region of the second layer comprises a barrier positioned on the second side of the second layer. In some embodiments, the at least one sensor is positioned between the barrier and the hydrophilic portion of the second layer.

In some embodiments, at least one of (a) the first layer or (b) the second layer includes a fluoropolymer. In some embodiments, the fluoropolymer includes expanded polytetrafluoroethylene.

In some embodiments, the detector also includes an adhesive positioned on at least a portion of the first side of the first layer, the adhesive being configured to adhere the first layer to the skin.

In some embodiments, an average pore size of the first layer is from 0.04 to 200 µm. In some embodiments, an average pore size of the first layer is from 0.1 to 5 µm. In some embodiments, an average pore size of the second layer is from 0.03 to 10 µm. In some embodiments, an average pore size of the second layer is from 0.03 to 5 µm.

In some embodiments, a bubble point of the first layer is from 0.3 to 1500 kPa. In some embodiments, a bubble point of the first layer is from 5 to 500 kPa. In some embodiments, a bubble point of the second layer is from 5 to 2000 kPa. In some embodiments, a bubble point of the second layer is from 100 to 1000 kPa.

In some embodiments, a bubble point of the second layer is from 1.1 to 1000 times greater than a bubble point of the first layer. In some embodiments, a bubble point of the second layer is from 2 to 100 times greater than a bubble point of the first layer. In some embodiments, a bubble point of the second layer is from 1 to 1500 kPa greater than a bubble point of the first layer. In some embodiments, a bubble point of the second layer is from 5 to 500 kPa greater than a bubble point of the first layer.

In some embodiments, the first layer and the second layer are at least partially bonded to one another.

In some embodiments, the sensors are one of (1) printed onto the at least one of (a) the first layer or (b) the second layer, (2) physically retained in proximity to the at least one of (a) the first layer or (b) the second layer, (3) deposited onto the at least one of (a) the first layer or (b) the second layer, (4) adhered to the at least one of (a) the first layer or (b) the second layer, or (5) sandwiched between the first layer and the second layer.

BRIEF DESCRIPTION OF THE DRAWINGS

The accompanying drawings are included to provide a further understanding of the disclosure and are incorporated in and constitute a part of this specification to illustrate embodiments. Together with the description the drawings serve to explain the principles of the disclosure. The accompanying drawing figures referred to herein are not necessarily drawn to scale, but may be exaggerated to illustrate various aspects of the present disclosure, and in that regard, the drawing figures should not be construed as limiting.

DETAILED DESCRIPTION

Figure 1:
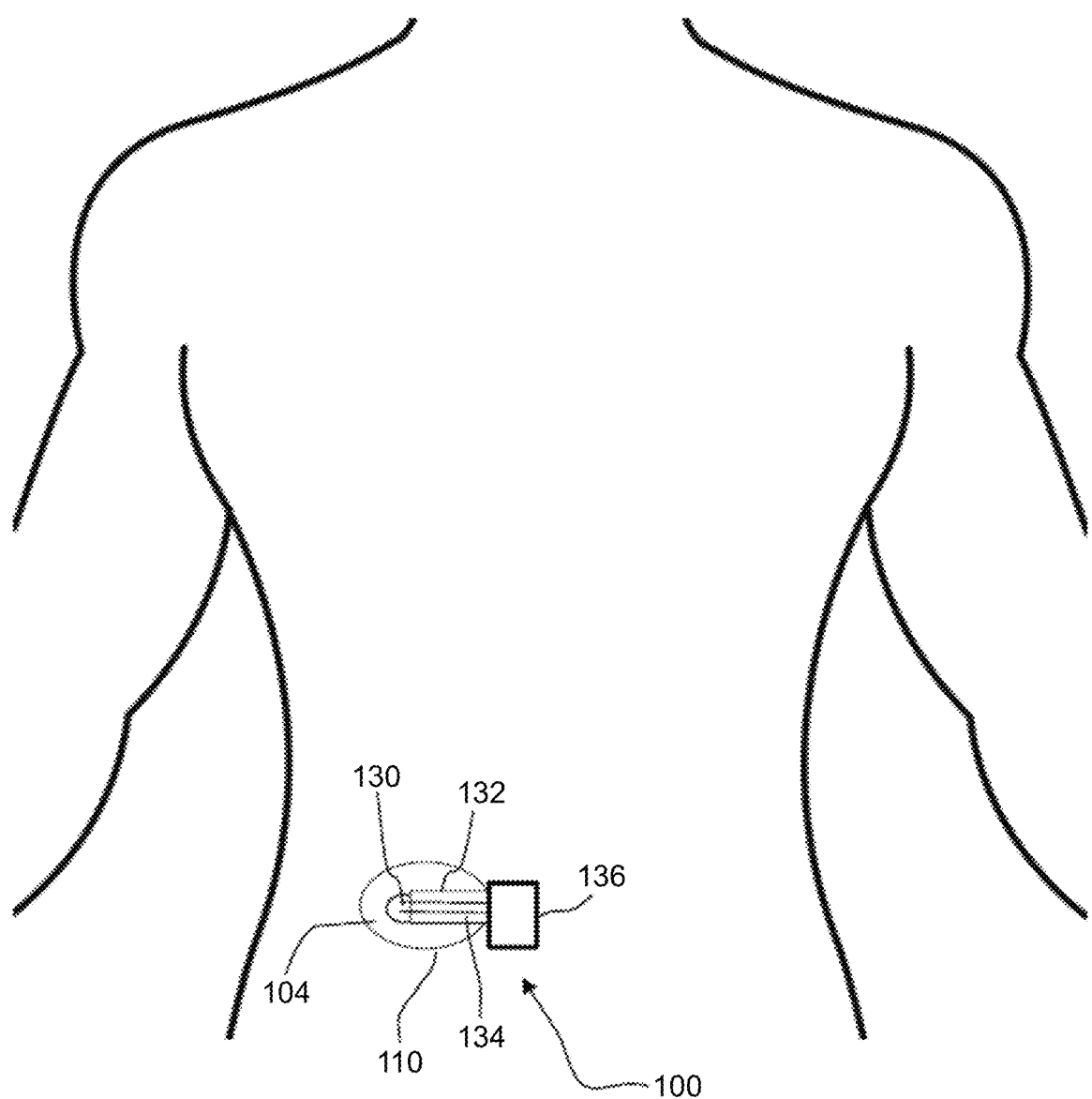
FIG. 1 is a schematic of a detector attached to a person in accordance with embodiments disclosed herein.

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the drawing figures should not be construed as limiting.

Devices and Methods

Disclosed herein are detectors for detecting one or more analytes in a sample. The sample is collected in a porous material. One or more sensors are adjacent to the porous material and are adapted to provide a response to the presence of an analyte in the sample. Advantageously the porous material collects a sample having a low flow rate and laterally displaces the sample over a large area that enhances detection. This allows the detector to have access to a sufficient volume of sample. In some embodiments, the porous material continuously collects samples to displace older samples with fresh samples.

The detectors described herein are useful for analyzing bodily fluids such as sweat, blood, urine, saliva, interstitial fluid, or other bodily fluids. These bodily fluids contain small but quantifiable percentages of analytes, also referred to as biomarkers. These bodily fluids may contain various analytes such as an ion, a protein, a cytokine, a peptide, an enzyme, a metabolite, a hormone, or DNA. An increase in various cytokines, for example, could be representative of trauma, infection, or cancer. The detectors described herein are not limited to use with bodily fluids, and may alternatively be useful for analyzing any fluid that may contain an analyte of interest. The detector may be used in a non-invasive manner that collects the sample while on a person's skin, or it may be used to collect samples from other surfaces, such as in forensics. For example, the detectors may be useful for analyzing blood sugar levels or sweat rates for hydration monitoring. Sweat rate may be measured in real time, for example by detecting sodium and/or chloride ions in the sample. Additional medical uses for the detectors disclosed herein include medical uses such as monitoring and detection of cystic fibrosis, renal disease, or cardiovascular diseases.

Although the present invention may be used with several different bodily fluids, for purposes of clarity this disclosure will discuss the embodiments in terms of collecting sweat from a user.

Some fluid samples to be analyzed may be available in very small volumes. For example, sweat may contain analytes of interest, but the volume of sweat available for analysis varies depending on activity level, environment, and individual physiology. Previous efforts have found difficulty in collecting a volume suitable for analysis or have required a volume that exceeded a person's ability to produce sweat. While a person participating in strenuous activity may perspire heavily, e.g., over 1 nL per minute per gland, a person who is sedentary may perspire very little, e.g., under 1 nL per minute per gland. Similarly, infants, elderly individuals, or individuals in cooler environments may perspire very little. It should be understood that perspiration rates vary between people as well as between different locations on the same person. To provide a sufficient volume of a sample, the porous material as described herein is capable of collecting a sample from a low flow rate, e.g., from 0.1 to 5 nL per minute per gland, and laterally displacing the sample over a suitable area, which is useful for enhancing detection, leading to improvements in sensing analytes. Each detector may have a different target area that is beneficial for sample detection. In particular, the embodiments described herein may be particularly useful to achieve target areas that are 20 mm$^2$ or more, e.g., from 20 to 70 mm$^2$. In some embodiments, the target area may be smaller as needed for the sensors.

In addition to providing a suitable area of sample, the lateral displacement in of the sample in the porous material is rapid and allows the detectors to provide fast response times. This leads to improvements in detection and reduces a loss in sensitivity due to delays. In one embodiment, the lateral displacement of the sample to the target area is within a few minutes, such as less than 20 minutes, or less than 10 minutes or less than 5 minutes.

When used to collect sweat on a person's skin the porous material can rapidly uptake sweat and prevent pooling of sweat on the skin surface. Pooling causes user discomfort and may further cause difficulties in adhering the detector to the skin. After the sweat is laterally displaced, the sweat may evaporate from the porous material. The rate of evaporation should allow sufficient time for the sensors to detect the analytes of interest. This further reduces excessive pooling and provides a replenishment with fresh sweat. Fresh sweat refers to sweat that is more recently secreted from a user and is understood to have analytes that reflect a user's present physical condition more accurately than earlier secreted sweat. After the sweat is secreted, the sweat ages, which reduces its effectiveness at providing a useful sample for detection. The porous material described herein provides moisture control to allow the sensors to receive fresh sweat over a large area. As further embodiments will describe, the porous material can provide a constant flow of fresh sweat to the sensor as well as reduce the comingling of fresh sweat with earlier secreted sweat.

In a first embodiment, a detector as described herein includes a porous material for collecting a fluid, wherein the porous material includes at least one wettable layer, or more particularly a hydrophilic layer. The porous material has a sample-collection surface and an analyte-detection surface. There are one or more sensors mounted to the analyte-detection surface. The sample is drawn through the sample-collection surface and laterally displaced so that sensors can contact a sufficient area of the sample in the analyte-detection surface.

In some embodiments, the one or more sensors are physically held in contact with the analyte-detection surface (e.g., with a clamp, clip, or other similar mechanical engagement). In some embodiments, the one or more sensors are printed (e.g., screen-printed) onto the analyte-detection surface. In some embodiments, the one or more sensors are deposited onto the analyte-detection surface. In some embodiments, the one or more sensors are adhered to the analyte-detection surface (e.g., using an adhesive). In some embodiments, the one or more sensors are held in proximity to the analyte-detection surface by being sandwiched between two adjacent layers of the fluid-collecting porous material.

A suitable porous material for use herein has the ability to transmit fluids through the internal voids, i.e. pores, when the material is subjected to a differential pressure or concentration across it and is characterized by a Gurley number of 300 sec or less. In some embodiments, a porous material described herein is characterized by a Gurley number of 50 sec or less, 10 sec or less, or 1 sec or less. The term porous indicates presence of voids, but not a specific size of voids within a material. There are many techniques by which to measure pore size, including but not limited to bubble point, mean flow pore size, liquid entry pressure, porosimetry, and image analysis with SEM, MicroCT, or other imaging tools. The presence of voids can be determined with or without the use of magnification, as appropriate, and may optionally be determined by the removal of materials that fill the voids.

In one embodiment, the porous material may include two or more porous layers. An asymmetric configuration, with larger average pore size in regions that collect the sample fluid and smaller average pore sizes in regions adjacent to the sensor(s) may further laterally displace the sample. The two adjacent porous layers may be in fluid communication to allow the sample to pass between the layers. In addition, the porous material is wettable, e.g., hydrophilic, to retain the sample within the voids.

As indicated above, the porous material is wettable and may be referred to as being hydrophilic. This allows the porous material to be wetted with a liquid sample, and, in particular, sweat. The hydrophilicity of the porous material can be measured by surface energy. Surface energy may be measured in Dynes per centimeter (Dynes/cm) using ACCU DYNE TEST™ Marker Pens (DIVERSIFIED Enterprises). In one embodiment, the hydrophilic materials have a surface energy from 30 to 70 Dynes/cm. In contrast, hydrophobic materials may have a surface energy of less than or equal to 25 Dynes/cm, e.g., from 15 to 25 Dynes/cm. In contrast, hydrophobic materials repel the liquid sample, but may allow vapors to pass through.

In some embodiments, the porous material collects the sample and conveys it through the porous material toward the one or more sensors. For example, the porous material may convey the fluid by capillary action. In some embodiments, a decrease in pore size from the sample-collection surface to the analyte-detection area provides a driving force for moving a sample fluid through the porous material by capillary action. In addition, the smaller pore size or tight microstructure, assists in lateral displacement of the sample near the sensors. The analyte-detection area acts as a reservoir for holding the sample for a sufficient time to allow analysis.

In some embodiments the wettability of the porous material varies across the material, such that with regard to a particular fluid, the porous material has high wettability in some areas and low or no wettability in other areas. For example, for an aqueous sample fluid, the porous material may include hydrophilic regions and hydrophobic regions. The various regions may further assist in controlling the flow of the sample through the porous material. In addition, hydrophobic regions may be used to control the evaporation of the sample after the detection.

In one embodiment, wettable and non-wettable regions may form a pattern on a surface of the porous material. The wettable and non-wettable regions may form a pattern through a cross-section of the porous material. Variation in wettability across and through the thickness of the porous material provides a flow path for a sample fluid through the material. For example, an aqueous sample of sweat may flow primarily or exclusively through the hydrophilic regions of a porous material and may not flow through hydrophobic regions of the same porous material. Thus, variation in hydrophilicity/hydrophobicity across and through the thickness of the porous material may provide a flow path for an aqueous sample through the material. In some embodiments, the wettable and non-wettable regions, or the hydrophilic and hydrophobic regions, of the porous material form microfluidic wettable or hydrophilic channels between the sample-collection surface and the analyte-detection surface.

For ease of description herein the terms hydrophilic and hydrophobic may be used to describe a porous material, but persons skilled in the art will understand that for a non-aqueous sample fluid those terms refer to the wettability of the porous material by the non-aqueous fluid.

The porous material includes a first surface and a second surface. The first surface may be a sample-collection surface and the second surface may be an analyte-detection surface. The first surface, referred to as a sample-collection surface, may be entirely hydrophilic or may include at least one hydrophilic region. The hydrophilic regions of the sample-collection surface function to absorb, or uptake, an aqueous sample, such as a bodily fluid, into the porous material, and the sample is then conveyed through the porous material to the analyte-detection surface.

To retain the sample, the second surface, referred to as an analyte-detection surface, may be entirely hydrophilic or may include at least one hydrophilic region. Although the first and second surface are hydrophilic, the relative degree of hydrophilicity may vary between the surfaces. Also, each surface may have hydrophobic regions. In some embodiments, one or more sensors are located in or on a hydrophilic region of the analyte-detection surface.

In some embodiments, a detector described herein include a porous material that includes at least two adjacent porous layers wherein a first layer includes the sample-collection surface and a second layer includes the analyte-detection surface and wherein the sample collection surface and the analyte-detection surface are in fluid communication. The two adjacent layers may both be hydrophilic porous layers wherein a first hydrophilic layer includes the sample-collection surface and a second hydrophilic layer includes the analyte-detection surface and wherein the sample collection surface and the analyte-detection surface are in fluid communication. In some embodiments, the first and second layers each include pores, wherein the average pore size of the first layer is larger than the average pore size in the second layer. This makes the second layer tighter and allows lateral displacement of the sample. In addition, the more open pores in the first layer allow the sample to diffuse through the layer and into the second layer. In some embodiments, where the pore size of the first layer is larger than the pore size of the second layer, the second layer may have a bubble point of 65 kPa or more, e.g., 100 kPa or more, 150 kPa or more, or 175 kPa or more. In terms of ranges, the bubble point of the second layer is from 65 to 1500 kPa, e.g., from 150 to 1000 kPa or from 175 to 500 kPa. In one embodiment, the bubble point of the second layer is greater than the first layer. In some embodiments where the pore size of the first layer is larger than the pore size of the second layer, the difference in bubble point of the first and second layers is 50 kPa or more. The difference in pore size may be attributed to the different microstructures of each layer.

In some embodiments of a detector including at least two adjacent porous layers, the first layer (e.g., a layer having large pores) has an average pore size that is from 0.04 to 200 µm, or from 0.5 to 10 µm, or from 0.1 to 5 µm, or from 0.25 to 1 µm, or from 0.35 to 0.4 µm. In some embodiments of a detector including at least two adjacent porous layers, the first layer has a bubble point that is from 0.3 to 1500 kPa, or from 2 to 1000 kPa, or from 5 to 500 kPa, or from 10 to 300 kPa, or from 150 to 200 kPa, or from 180 to 200 kPa. In some embodiments of a detector including at least two adjacent porous layers, the second layer (e.g., a layer having small pores) has an average pore size that is from 0.03 to 10 µm, or from 0.03 to 5 µm, or from 0.03 to 0.5 µm, or from 0.1 to 0.2 µm, or from 0.14 to 0.15 µm. In some embodiments of a detector including at least two adjacent porous layers, the second layer has an average bubble point that is from 5 to 2000 kPa, or from 50 to 1500 kPa, or from 100 to 1000 kPa, or from 200 to 800 kPa, or from 400 to 600 kPa. In some embodiments of a detector including at least two adjacent porous layers, the second layer has a bubble point that is from 1.1 to 1000 times the bubble point of the first layer, or from 2 to 100 times the bubble point of the first layer, or from 2 to 5 times the bubble point of the first layer, or from 2.5 to 3 times the bubble point of the first layer. In some embodiments of a detector including at least two adjacent porous layers, the second layer has a bubble point that is 1 to 1500 kPa greater than the bubble point of the first layer, or 5 to 500 kPa greater than the bubble point of the first layer, or from 50 to 400 kPa greater than the bubble point of the first layer, or from 300 to 350 kPa greater than the bubble point of the first layer.

In some embodiments with two layers, the two layers are bonded to one another. Any number of techniques may be used to bond together two or more layers of porous material. For example, the first and second layers may be adhered to each other, or to another layer or support structure, such as with a thermoplastic resin, elastomer, or other adhesive material, applied discontinuously so as to allow for the flow of fluid through the adhesive. Non-limiting examples of thermoplastic resins include, but are not limited to, fluorinated ethylene propylene (FEP), perfluoroalkoxy polymer resin (PFA), and tetrafluoroethylene hexafluoropropylene and vinylidene fluoride, polyvinylidene fluoride (PVDF) or combinations thereof. The adhesive may be applied as a surface coating or may be at least partially imbibed into the pores of one or both layers. Alternatively, the layers may be at least partially bonded together without the aid of an adhesive using techniques including, but not limited to, heat fusion, sintering, and the like. In some embodiments, two layers that are coated with a hydrophilic coating (e.g., EVOH) are bonded together by the hydrophilic coating. In some embodiments, such layers are bonded by coating with the hydrophilic coating and layering at the same time.

Without intending to be limited by any particular theory, skin is nonplanar, consisting of peaks and valleys, and typically has a peak-to-valley height on the order of 60 µm. In embodiments with two layers, the layer in contact with the skin surface may be conformable to increase the collection of sweat and decrease pooling under the layer. Conforming to the skin decreases the void area between the skin surface (e.g., the surface of the skin at the valleys) and layer. Minimizing the dead volume of sweat between the detector and skin surface advantageously allows measurements to be taken on a smaller quantity of sweat. Reducing dead volume, isolating sweat pores, minimizing irritation, and other aspects are all desirable for prolonged stimulation of sweat for chronological monitoring applications. As a person perspires a sweat sample from the eccrine duct may pass directly through the sample collection surface and into the analyte-detection layer. Both layers for collecting the sample fluid are also flexible to conform closely to the skin. In one embodiment, the collection surface is part of a layer that is conformable and has a non-uniform thickness. The analyte-detection layer may also be flexible but generally has a consistent thickness to allow the lateral displacement of the sample. The collection surface layer is adjacent to the skin and may be conformable to reduce skin abrasion and allow a person to wear the detector throughout the day with minimal discomfort. To allow for a conformable layer, the first layer may be relatively thicker as compared to the second layer that includes the analyte-detection surface. Thus, in some embodiments, the first layer may have a variable thickness with an average thickness that is from 5 µm to 100 µm, or from 10 to 50 µm, or from 10 to 20 µm. In some embodiments, the first layer is sufficiently conformable so as to be capable of extending 10 µm into a 60 µm deep valley in the skin, or 20 µm into a 60 µm deep valley in the skin, or 30 µm into a 60 µm deep valley in the skin, or 40 µm into a 60 µm deep valley in the skin, or 50 µm into a 60 µm deep valley in the skin. In contrast to the first layer, the second layer may be relatively thin and generally more uniform. The second layer may also be very thin to reduce the size of the detector. In one embodiment, the second layer has a thickness from 0.1 to 50 µm, or from 1 to 30 µm, or from 1 to 20 µm, or from 1 to 10 µm, or from 1 to 5 µm. The second layer may include a mass to area ratio of 4 gsm or less. In some embodiments the entire fluid-collecting porous material includes a mass to area ratio 4 gsm or less, e.g., 3 gsm or less or 1 gsm or less. Incidentally, the membrane may have a mass per area ratio range from 0.5 gsm to 4 gsm, e.g., from 0.5 to 3 gsm.

In embodiments with a sample-collection layer and an analyte-detection layer, the detection layer may be adapted to displace a sample laterally through the detection layer. For example, a sample may be absorbed into pores of a collection layer through a sample collection surface opposite the analyte-detection layer, travel through the sample collection layer (e.g. by capillary action) to the analyte-detection layer, enter the analyte-detection layer at a first location, and then travel through the analyte-detection layer in a lateral direction from the first location to a second location. In some embodiments, the lateral direction is in-line with the surface of the analyte detection layer, and, in particular, parallel or horizontal.

The sample or the surface from which the sample is taken may have impurities or other non-analyte components that could contaminate the sample and prevent an accurate analysis of the target analyte. For example, a sample collected from skin may include skin cells, dirt, oil, hair, or other debris. Such contaminates may foul the sensors. In some embodiments, pores of the sample collection surface of the porous material filter undesirable components from a sample. For example, in some embodiments the sample-collection surface includes pores having a size small enough to filter 97% of particulates having a diameter of greater than 0.07 microns from the sample.

Materials useful as a porous material in the detectors described herein include but are not limited to fluoropolymers, polyurethanes, polyolefins, polyesters, polymeric organosilicon compounds, and copolymers, mixtures, and combinations thereof. In some embodiments, the porous material may include a fluoropolymeric material, such as polytetrafluoroethylene (PTFE); polyvinylfluoride (PVF); polyvinylidene fluoride (PVDF); perfluoroalkoxy (PFA); fluorinated ethylene-propylene (FEP); polychlorotrifluoroethylene (PCTFE); ethylene tetrafluoroethylene (ETFE); polyvinylidene fluoride (PVDF); ethylene chlorotrifluoroethylene (ECTFE), or a copolymer thereof. In some embodiments, the porous material may include an expanded fluoropolymer, such as expanded PTFE (ePTFE). In some embodiments, the porous material may include a modified PTFE polymer, an expanded polypropylene (ePP), an expanded polyethylene (ePE), or a copolymer thereof. Useful ePTFE materials may have a microstructure comprising nodes, fibrils, and voids between the nodes and fibrils. For purposes of this disclosure, materials useful for the microporous layer do not include textiles or fibrous layers created from microporous fibers, such as paper. Although paper has a high capacity it tends to be too thick and does not adequately displace a small volume of a sample.

The first layer may have an ePTFE material having a microstructure of elongated nodes interconnected by fibrils which form a structural network of voids or pores through the spaces between the nodes and fibrils, which voids or pores extend through the thickness of the membrane and from one side of the membrane to the other. This provides a very open microstructure. In one embodiment, nodes may be aligned in substantially elongated parallel configurations. These aligned elongated nodes are interconnected along their length by a myriad of microfibrils. The result is a series of rib-like rows of nodes, with each row connected by a multitude of fibrils. A suitable ePTFE material for the first layer is described in U.S. Pat. No. 5,814,405 and International Patent Application Publication No. WO2004/079208, the contents of both of which are incorporated herein in their entirety.

The second layer may have an ePTFE material with a tighter microstructure as compared with the first layer. A suitable ePTFE material for the first layer is described in U.S. Pat. No. 7,306,729, the contents of which are incorporated herein by reference in their entirety.

Materials useful as a porous material in the detectors described herein may not be inherently hydrophilic or inherently hydrophobic, but may be made partially or entirely hydrophilic or hydrophobic as desired by use of appropriate treatments and/or coatings. For example, an ePTFE membrane is hydrophobic, but can be made hydrophilic (or made to have hydrophilic regions) by applying a coating. One example of such a coating is ethylene-vinyl alcohol copolymer (EVOH) sold commercially as Soarnol™. A suitable ePTFE with a hydrophilic coating is further described in U.S. Patent Application Publication No. 2013/0112621 A1, the contents of which are incorporated herein by reference in their entirety. A functional TFE copolymer having a comonomer with a functional group, such as perfluoro (8-sulfonic acid fluoride-5-methyl-3,6-dioxa-1-octene) (PSVE), may also provide a suitable hydrophilic porous material. Another suitable ePTFE material that has hydrophilic properties is described in U.S. Pat. No. 9,139,669, the contents of which are incorporated herein by reference in their entirety.

As described herein the porous material captures the sample and laterally displaces the sample. In one embodiment, the porous material has a porosity of from about 40% to about 98%, e.g. 70 to 90%, including any coating. Although previously used materials such as desiccants and hydrogels can wick the sample, these structures are not sufficiently porous. Thus, in one embodiment the porous material does not include hydrogel. A hydrogel may cause sensor inaccuracy because it is difficult to replenish with fresh sweat.

Materials described above useful as a porous material in the detectors described herein are not dissolvable in water. In some embodiments, a porous material useful in a detector disclosed herein includes materials not dissolvable in water. In some embodiments, a porous material useful in a detector disclosed herein includes only materials not dissolvable in water. In some embodiments, a sample-collection surface and/or an analyte detection surface as disclosed herein includes a material not dissolvable in water. In some embodiments, a sample-collection surface and/or an analyte detection surface as disclosed herein includes only materials not dissolvable in water. In some embodiments, a fluid sample is collected directly into the detector without passing through a volume of oil.

The detectors described herein may be adapted to facilitate flow of a sample fluid through the detector. For example, patterned hydrophilic/hydrophobic regions can be used to form pathways, such as microfluidic channels, through which the sample fluid flows. Liquid barrier regions or layers provide another means of facilitating fluid flow in a desired direction. Liquid barrier regions can be used to direct sample fluid flow through a detector where the porous material is entirely hydrophilic or where the fluid flow is further directed by patterned hydrophilic/hydrophobic regions.

In some embodiments, a liquid-proof barrier covers a portion of an analyte detection surface and one or more sensors. A liquid-proof barrier layer can slow or prevent evaporation of a sample fluid from a surface at and around a sensor.

In some embodiments, a liquid proof barrier layer can be used to direct sample flow past a sensor to continually provide fresh sample for real-time analysis of a sample. As one example, if a liquid proof barrier covers a region of an analyte detection surface, leaving another region uncovered and open to the external environment, a sample fluid will be able to evaporate from the uncovered region, but unable to evaporate from the covered region. As sample fluid evaporates from the uncovered region, additional sample will flow from the covered region into the uncovered region (e.g. by capillary action). Thus, the detector includes a pathway for the sample fluid. When one or more sensors are placed in that pathway, the sensors can detect change in concentration of an analyte over time.

A liquid-proof barrier can be formed by any suitable polymeric material or resin. In particular, hydrophobic polyurethane and fluoropolymer membranes, acrylates, and silicones may be used as the liquid-proof barrier layer. A person skilled in the art could determine a suitable polymer or resin for use as a liquid-proof barrier for a specific application.

The detectors described herein include one or more sensors adapted to provide a response to the presence of an analyte in a sample. The sensors can include electrodes. In some embodiments, the analyte may be an ion, cytokine, protein, peptide, metabolite, glucose, glucose oxidase, enzyme, hormone, or DNA. For example, the analyte could be any analyte of interest including, but not limited to, lactate, ethanol, cortisol, urea, glucose, orexin-A, neuropeptide Y, Cytokine, $Na^+$, $K^+$, $Cl^-$, or $NH_4^+$. In some embodiments, the sensors are adapted to provide a response to a pH, temperature, humidity, or impedance.

The sensors can include a variety of analyte probes or electrical sensing methods useful in embodiments of the present invention. A plurality of electrodes or arrangements are possible or an array of sensors may be used. In one embodiment, the sensor may have an electrode coated with an ion-selective membrane and a reference electrode. In one embodiment, the sensor may have at least three electrodes that are spaced-apart: a reference electrode, a working electrode, and a counter electrode. The reference electrodes may be made of silver chloride. Laterally displacing the sample over a target area allows sufficient volume of the sample to be in contact with the spaced-apart electrodes. In some embodiments, a sensor includes at least one electrode that extends laterally and/or linearly along a portion of the analyte detection surface. Some sensor types, such as impedance, amperometric, or others, require fluid to make an electrical contact between two electrodes. In other embodiments, by way of example, a probe or electrical sensing method may be an aptamer, redox couples, an antibody layer, an enzyme layer, or an ionophore membrane. Further, a surface that is selective in some way for sensing without a specific probe layer (e.g., stripping voltammetry) may be used. Generally, any surface that provides an electrical response to the presence of an analyte is adequate for use in embodiments of the detectors disclosed herein. Even surfaces that utilize an insulator on an electrically conductive surface, such as electrical capacitance or field-effect type sensors, are included since they also have an electrically conductive surface, and hence have an electrical response (be it direct or indirect) to the presence of an analyte. In some embodiments, one or more sensors are located on the surface of a porous material, for example on an analyte detection surface.

The sensors include all known variations of biosensors. The description herein shows sensors as simple individual elements. The sensors may be connected to suitable electronics and may include, for example, such components as an electronics controller, communication circuit, memory, microcontrollers, transmitters, receivers, antennas, and other electronics useful in wearable sensors. If needed, a power source may also be included with the detector. The details of the electronics are not limiting for the purposes of the present disclosure.

In some embodiments, one or more sensors itself is porous. Porous electrodes may be, for example, a thin metal film that is porous, a fine metal wire mesh, or a porous layer of carbon nanotubes.

To reduce skin irritation, the detectors may not require sweat stimulation to generate sufficient volume of sweat for analysis. Prolonged stimulation of sweat can be problematic for some hyper sensitive individuals and can be avoided by the porous material disclosed herein. In other embodiments, the detectors described herein may include a heater for stimulating sweat to collect a sample fluid. In other embodiments, sweat stimulation may be applied by chemical, iontophoresis, electrical, or other mechanisms.

In some embodiments the detectors described herein may be adhered to a surface comprising a sample. For example, the detectors may be adhered to skin for collecting and analyzing sweat produced by the skin. Thus, a detector described herein may include a suitable adhesive that is formed in a continuous layer or a discontinuous layer, e.g. of dots or lines or grids. The adhesive may be on a portion of the sample collection surface, for example in a pattern, so the device may be adhered to a surface without impeding sample collection from that surface. The adhesive may be removable and replaceable so the detector is reusable. Without being limiting, suitable adhesives may be dermally acceptable, electrically conductive, insulating, permeable, impermeable, or have other various properties. Those skilled in the art will recognize that methods other than using adhesives to hold the detectors against skin may be used, such as but not limited to mechanical pressure, suction, embedding in clothing, braces or straps.

Turning now to the figures, FIG. 1 shows a detector 100 consistent with embodiments described herein in the form of a patch affixed to the abdomen of a user. It should be understood that the detector may be applied in various forms to different locations of a user. The detector 100 includes a porous material 110 that is adhered to the user with adhesive (not shown). The porous material 110 collects sweat (not shown) and displaces the sweat laterally in the region 104 of two sensors 130, which are adjacent to insulation 132 and connected by wires 134 to a suitable measurement circuit/device 136. In other embodiments, the device may be a wireless transmitter that connects to a remote device.

Figure 2A:
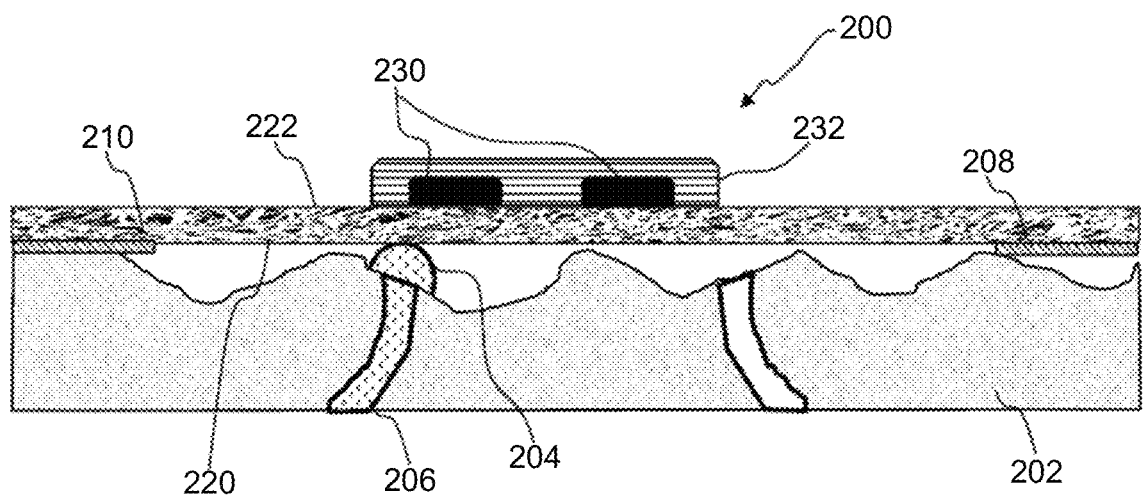
FIGS. 2A and 2B are cross-section views of a detector having a single porous material in accordance with embodiments disclosed herein
Figure 2B:
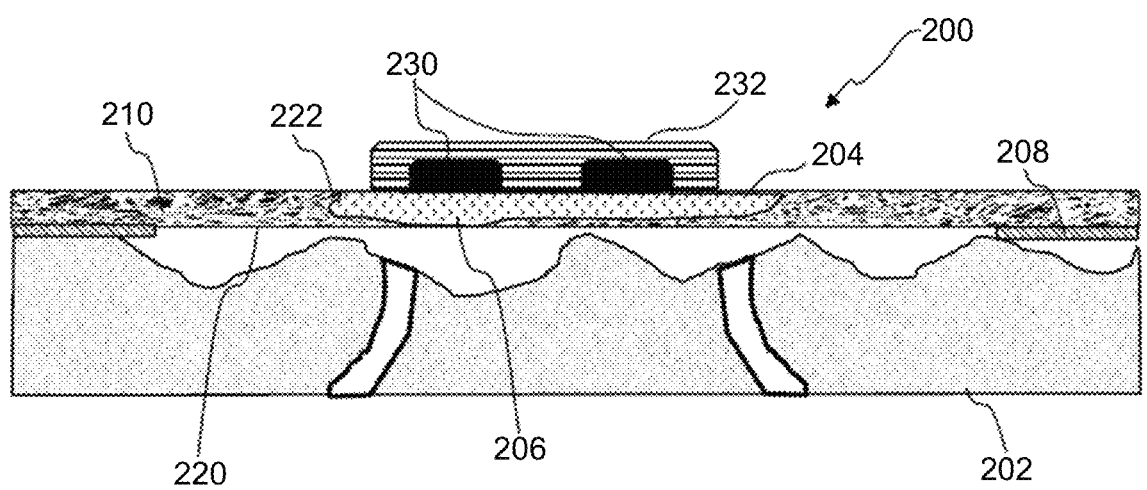

FIGS. 2A and 2B are cross-sectional views of a detector 200 placed on the surface of skin 202 to collect sweat 204 containing analytes 206. The detector 200 is adhered to the skin 202 by adhesive 208. The detector 200 includes a fluid-collecting porous material 210 comprising a sample-collection surface 220 and an analyte detection surface 222. The porous material 210 may be flexible to follow the contours in the skin 202. The fluid-collecting porous material 210 contacts, absorbs, and displaces the sweat 204. FIG. 2A shows the sweat 204 containing the analytes 206 as it is secreted from eccrine ducts in the skin 202 and contacts the sample-collection surface 220 of the fluid-collecting porous material 210. FIG. 2B shows the sweat 204 containing the analytes 206 after it is absorbed and displaced laterally by the porous material 210. The sweat 204 is near the two sensors 230. As analytes 206 are laterally displaced within the analyte-detection surface 222 that is in contact with sensors 230, a suitable measurement circuit (not shown) is able to detect charge transfer, changes in impedance, or other electrically measurable changes known by those skilled in the art that indicate the presence of analyte.

Although embodiments are shown with one or two porous layers, it should be understood that other embodiments may include additional porous layers.

Figure 3D:
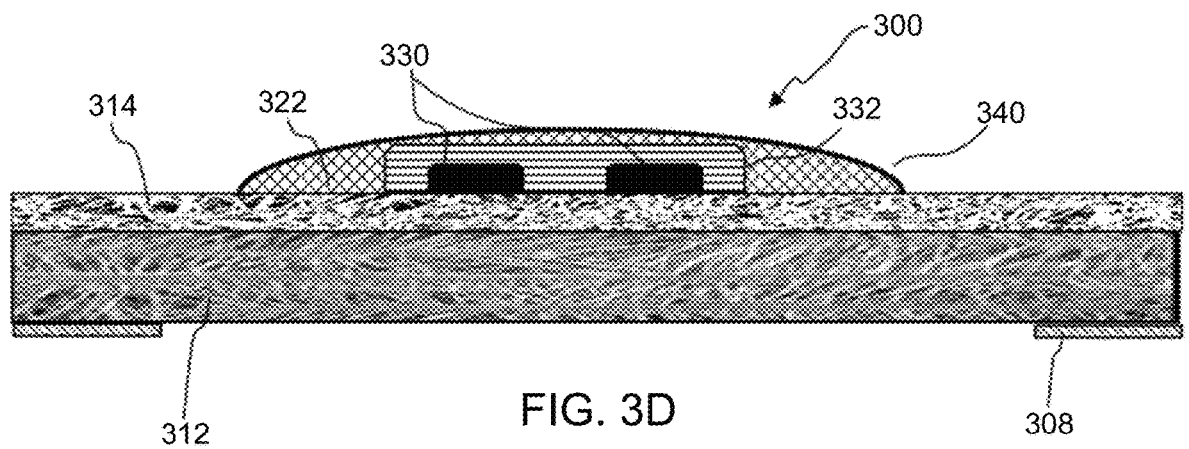
FIG. 3D is a cross-section view of the detector of FIG. 3A having a liquid barrier covering the target area in accordance with embodiments disclosed herein.
Figure 3A:
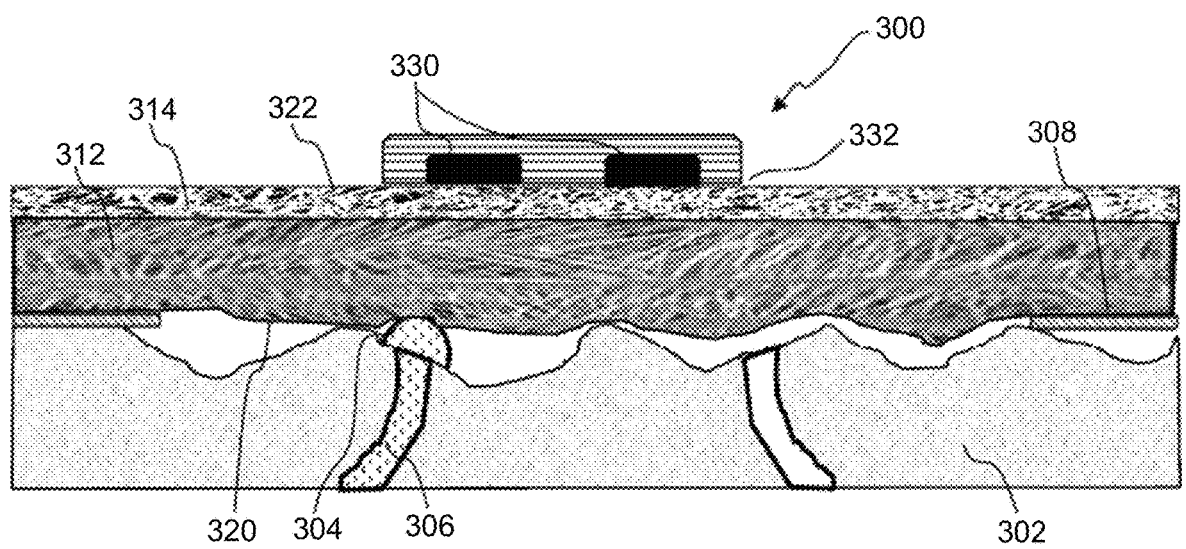
FIGS. 3A, 3B and 3C are cross-section views of a detector having a porous material with a first layer and a second layer in accordance with embodiments disclosed herein.
Figure 3B:
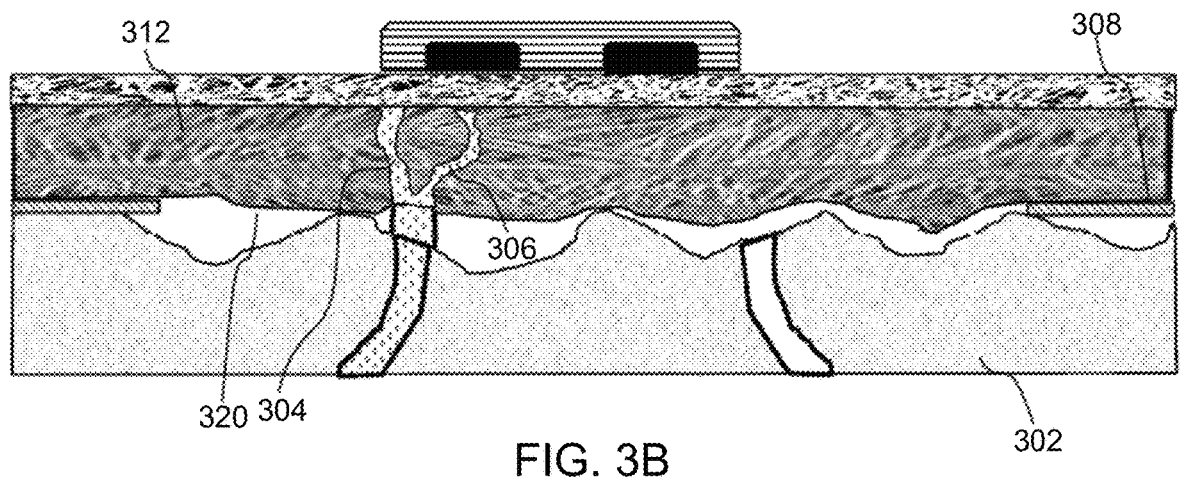
Figure 3C:
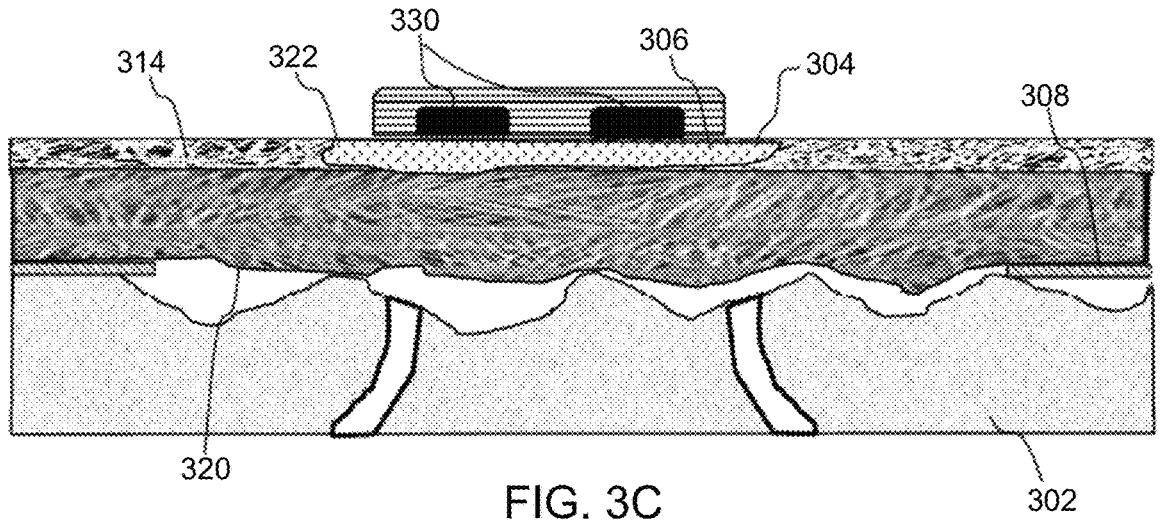

In other embodiments, the fluid-collecting porous material may include two or more porous layers. FIGS. 3A, 3B, and 3C are cross-sectional views of a detector 300 placed on the surface of skin 302 to collect sweat 304 containing analytes 306. The detector 300 is adhered to the skin 302 by adhesive 308. The detector 300 has a first porous layer 312 and a second porous layer 314. The first porous layer 312 includes a sample-collection surface 320 and the second porous layer 314 includes an analyte detection surface 322. The first porous layer 312 may be conformable to the skin 302. As shown the thickness of the first porous layer 312 may be non-uniform and may be compressed into the contours of the skin 302. The detector 300 further includes two sensors 330 mounted to the analyte-detection surface 322 and an insulation 332 for the two sensors 330 and are part of the analyte-detection surface 322. FIG. 3A shows the sweat 304 containing the analytes 306 as it is secreted from the skin 302 and contacts the sample-collection surface 320 of the first porous layer 312.

FIG. 3B shows the sweat 304 containing the analytes 306 after it is absorbed into the first porous layer 312 and as it traverses the first porous layer 312 from the sample collection surface 320 to the second porous layer 314. Due to the open pore structure, the sample rapidly transverses the layer through one or more pathways, e.g. microfluidic pathways. It should be understood that when there are multiple sweat glands in contact with the sensor that there may be several pathways from each sweat gland.

FIG. 3C shows the sweat 304 containing the analytes 306 after it is absorbed into and displaced laterally by the second porous layer 314. As analytes 306 are laterally displaced within the second porous layer 314 and are in contact with sensors 330, a suitable measurement circuit (not shown) is able to detect charge transfer, changes in impedance, or other electrically measurable changes known by those skilled in the art that indicate the presence of analyte. The rate of evaporation from the second porous layer 314 allows sufficient time for the sensors 330 to detect the analytes.

Figure 2C:
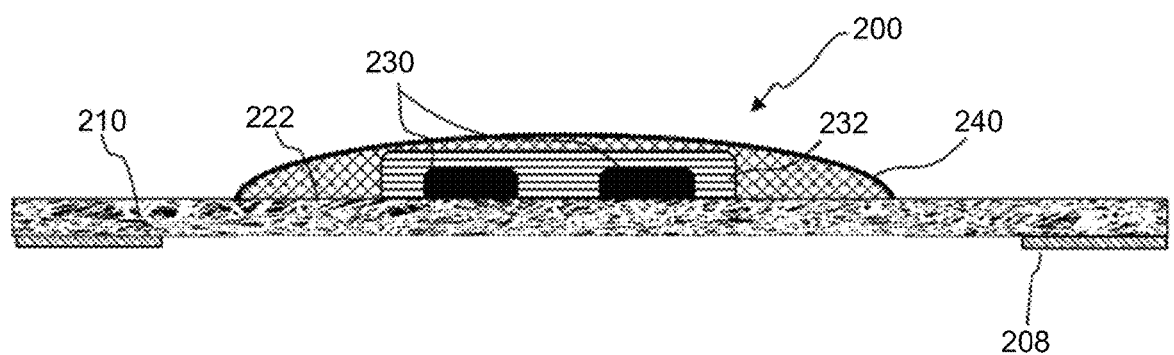
FIG. 2C is a cross-section view of the detector of FIG. 2A having a liquid barrier covering the target area in accordance with embodiments disclosed herein.

A liquid-proof layer may be positioned over the sensors. As shown in FIG. 2C, liquid-proof layer 240 covers the sensors 230. Likewise, in FIG. 3D, liquid-proof layer 340 covers the sensors 330. This barrier layer prevents egress of water from the outside environment which may result in a poor or false reading. In addition, the liquid-proof layer encourages the lateral displacement of the sample within the second porous layer by reducing evaporation. The liquid-proof layer may or may not be transparent in some embodiments. In further embodiments, the liquid-proof layer may cover the entire surface of the second porous layer. Liquid-proof layers may also be adjacent the edges of the porous material.

Figure 4:
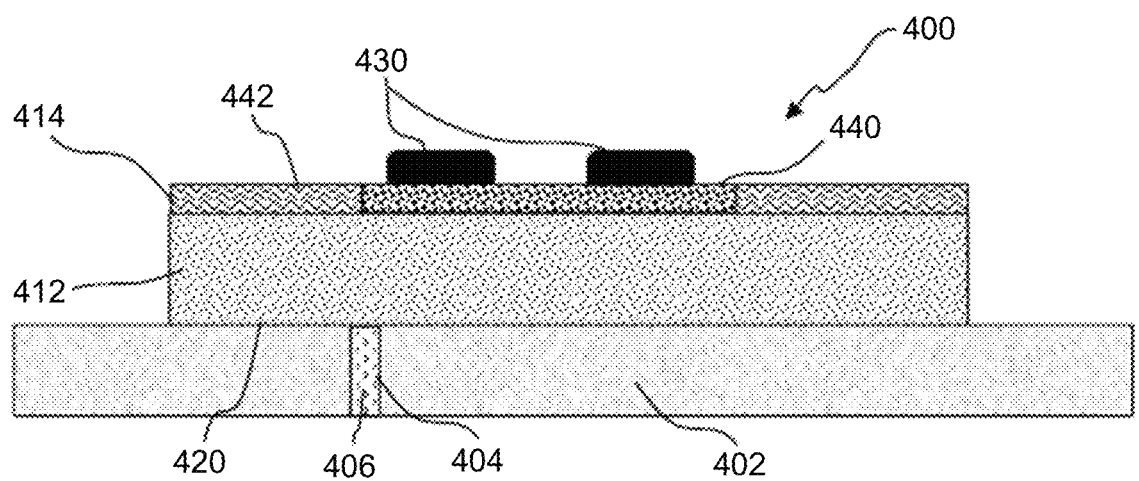
FIG. 4 is a cross-section view of a detector having a layer with hydrophilic and hydrophobic regions in accordance with embodiments disclosed herein.

FIG. 4 is a cross-sectional view of a detector 400 mounted on the surface of skin 402 to collect sweat 404 containing analytes 406. The detector 400 includes a sample collection layer 412 and a reservoir layer 414 that are in fluid communication with each other. The sample collection layer 412 includes a sample-collection surface 420 opposite the reservoir layer 414. The reservoir layer 414 includes a hydrophilic region 440 and a hydrophobic region 442 surrounding the hydrophilic region 440. The hydrophobic region 442 may partially or completely surround the hydrophilic region 440. The detector 400 further includes two sensors 430 mounted to the hydrophilic region 440 of the reservoir layer 414. As the sample is laterally displaced through the hydrophilic region 440, the hydrophobic region 442 prevents liquid water entry. However, the vapor may be evaporated through the hydrophobic region 442 to the external environment. This can facilitate the replenishment of the sweat in the hydrophilic region 440.

Figure 5:
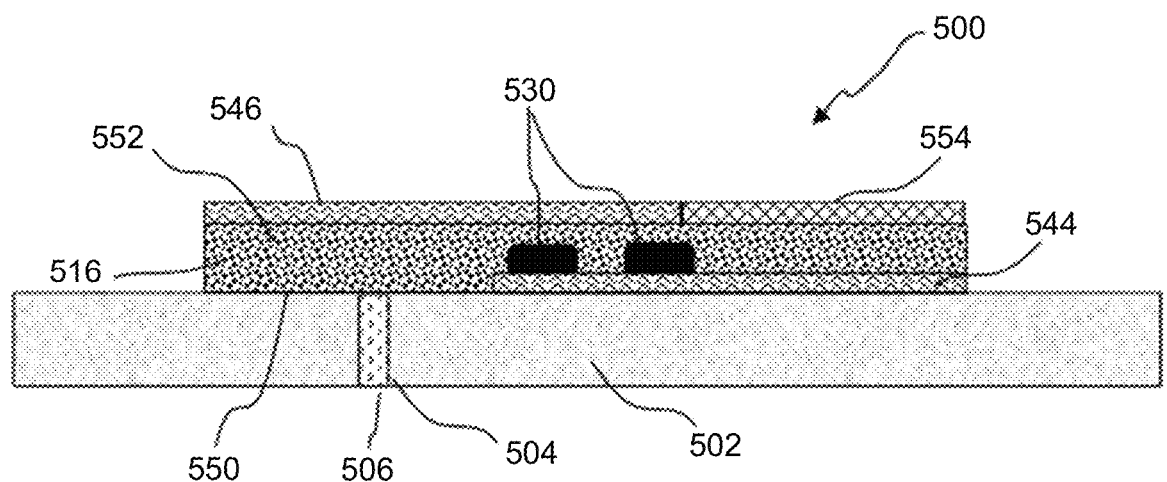
FIG. 5 is a cross-section view of a detector having sensors within the hydrophilic layer and mounted on a hydrophobic layer in accordance with embodiments disclosed herein.

FIG. 5 is a cross-sectional view of a detector 500 mounted on the surface of skin 502 to collect sweat 504 containing analytes 506. The detector 500 includes a hydrophilic porous material 516, a hydrophobic barrier 544 between a portion of the hydrophilic porous material 516 and the skin 502, an evaporation barrier 546 covering a portion of the hydrophilic porous material 516 opposite the hydrophobic barrier 544, and two sensors 530 mounted between the hydrophilic porous material 516 and the hydrophobic barrier 544. The hydrophobic barrier 544 and evaporation barrier 546 are off-set so that the portion of the hydrophilic porous material 516 that contacts the evaporation barrier 546 and the skin 502 but not the hydrophobic barrier 544 forms a sample collection zone 550; a second (middle) portion of the hydrophobic porous material 516 that contacts both the hydrophobic barrier 544 and the evaporation barrier 546 forms a pathway 552; and a third portion of the hydrophobic porous material 516 that contacts the hydrophobic barrier 544 but not the evaporation barrier 546 forms an evaporation zone 554. The two sensors 530 are located in the pathway 552 of the hydrophilic porous material 516. In use, the sweat 504 containing analytes 506 enters the fluid-collecting porous material 516 at the sample-collection zone 550, traverses the pathway 552, contacts one or more of the sensors 530, and exits the hydrophilic porous material 516 by evaporating at the evaporation zone 554.

Figure 6:
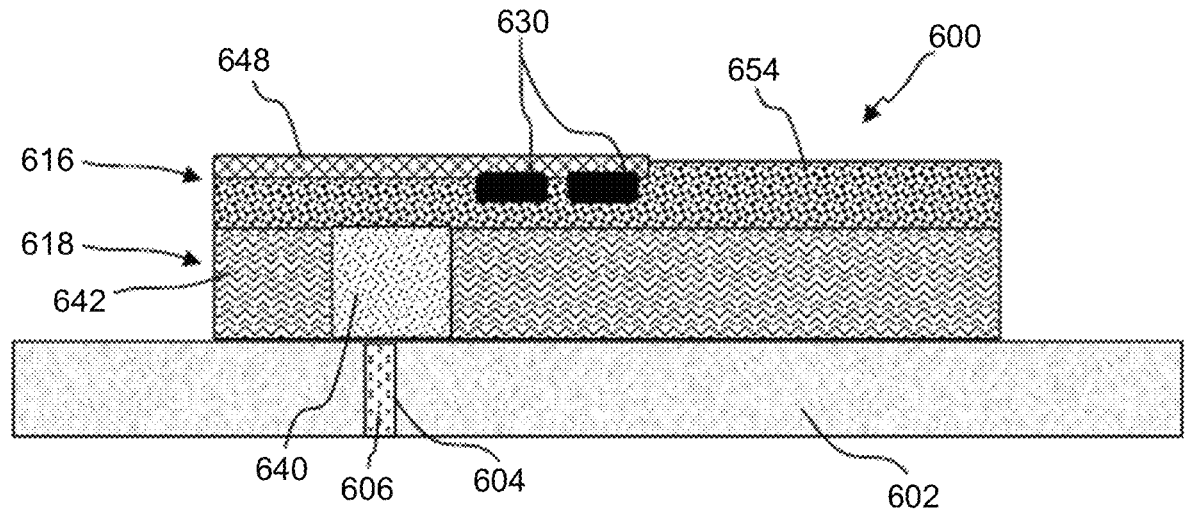
FIG. 6 is a cross-section view of a detector having a first layer with hydrophobic and hydrophilic regions in accordance with embodiments disclosed herein.

FIG. 6 is a cross-sectional view of a detector 600 mounted on the surface of skin 602 to collect sweat 604 containing analytes 606. The detector 600 includes a patterned porous layer 618 and a hydrophilic porous layer 616. The patterned porous layer 618 has hydrophilic regions 640 and hydrophobic regions 642. The hydrophobic regions 642 prevent egress of sweat and allow the detector to be positioned over a particular sweat gland. The detector 600 further includes a liquid barrier layer 648 on a first portion of the hydrophilic porous layer 616 opposite the patterned porous layer 618, an evaporation region 654, and at least one sensor 630 on the hydrophilic porous layer 616 between the liquid barrier layer 648 and the evaporation region 654. In use, sweat 604 containing analytes 606 enters the hydrophilic region 640 of the patterned porous layer 618, is laterally displaced throughout the hydrophilic region 640 past the sensor 630 and toward the evaporation region 654, and exits the hydrophilic porous layer 616 by evaporating at the evaporation region 654. Although one hydrophilic region 640 is shown in FIG. 6, in further embodiments there may be multiple hydrophilic regions to provide a pathway for the collected sweat to enter into the hydrophilic porous layer 616.

Although not shown in FIGS. 4-6, there may be an adhesive layer as described herein to attach the detector to skin.

Any detector disclosed herein may further include a liquid-proof barrier covering a portion of the analyte detection surface and one or more sensors.

Figure 7A:
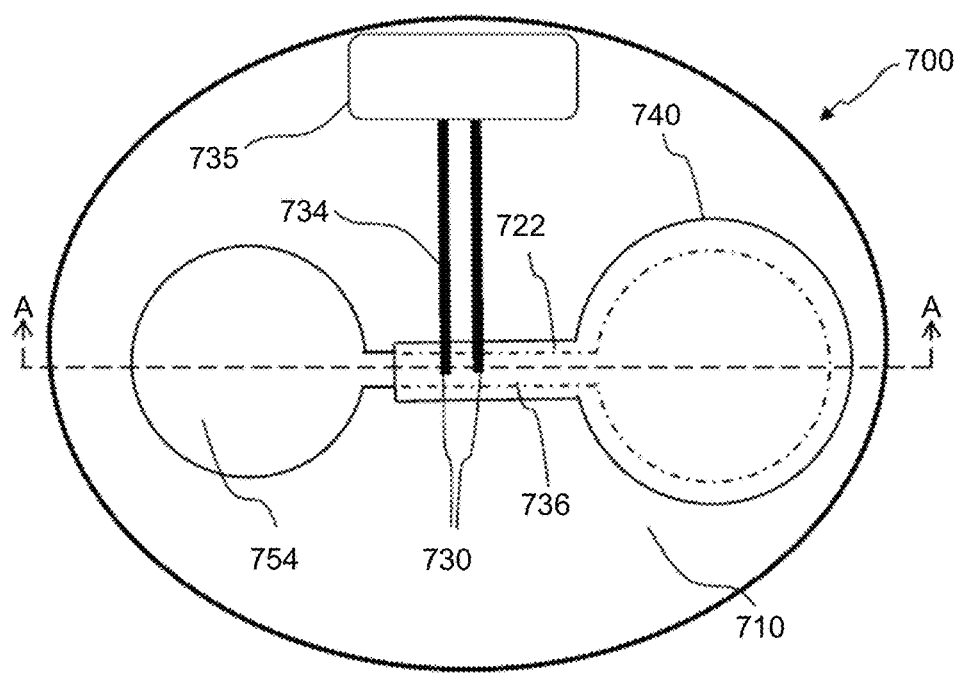
FIG. 7A is a top view of a detector having a flow path in accordance with embodiments disclosed herein.

In one embodiment, the detector may provide a flow path, or pathway, for a sample fluid. FIG. 7A is a top view of a detector 700 having a pathway for the sample to flow through. The detector includes two sensors 730 connected by wires 734 to a suitable measurement circuit/device 735. Although not shown, wires 734 may be mounted on an insulation material. The detector 700 further includes a liquid-proof barrier 740 covering the sensors 730 and part of an analyte detection surface 722. For purposes of illustration, the liquid-proof barrier 740 is shown as transparent. The liquid-proof barrier 740 prevents evaporation of a liquid sample and thus facilitates the flow of the sample through the pathway 736 to an uncovered evaporation region 754. The pathway provides a fluid connection between a collection zone and an evaporation zone. This allows the sweat to be replenished and provides a fresh sample for the sensors to detect the presence of analytes.

Figure 7B:
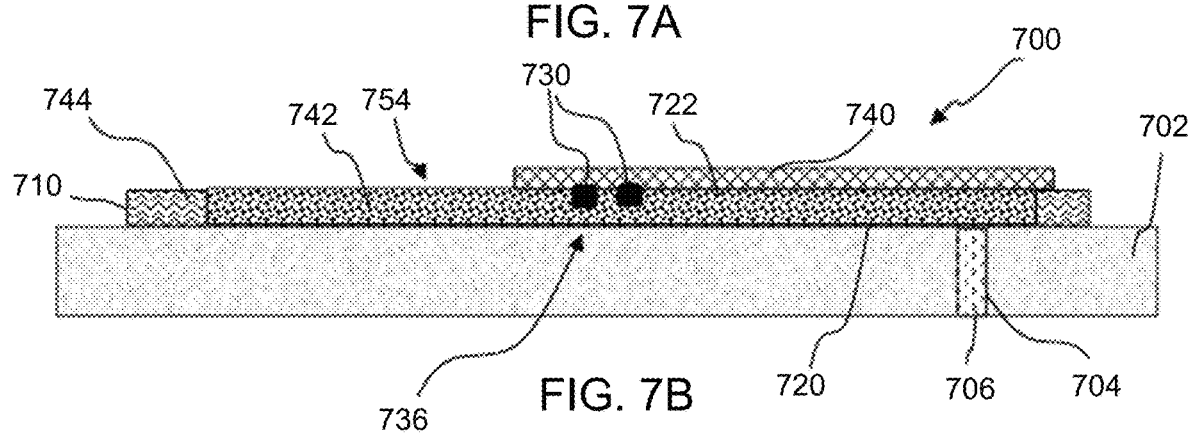
FIG. 7B is a cross-section view of the detector in FIG. 7A having one porous layer in accordance with embodiments disclosed herein.

FIG. 7B is a cross-sectional view of one embodiment of detector 700 along line A-A. FIG. 7B shows an embodiment having only a single porous layer. In FIG. 7B, the detector 700 is mounted on the surface of skin 702. The detector 700 includes a fluid-collecting porous material 710 comprising a sample-collection surface 720 and an analyte detection surface 722, and the detector 700 further includes a hydrophilic region 742 and a hydrophobic region 744 surrounding the hydrophilic region 742. The detector 700 further includes two sensors 730 mounted on pathway 736. A liquid-proof barrier 740 covers the two sensors 730 and portion of the analyte-detection surface 722 to form a collection zone. The liquid-proof barrier 740 prevents evaporation of a liquid sample and thus facilitates lateral displacement of a sample within the analyte detection surface to the evaporation zone. Detector 700 further includes an uncovered evaporation region 754. In use, sweat 704 containing analytes 706 enters the fluid-collecting porous material 710 below the liquid-proof barrier, traverses the hydrophilic region 742 of the fluid-collecting porous material 710 past the sensors 730 to the evaporation region 754, and exits the fluid-collecting porous material 710 by evaporating at the evaporation region 754.

Figure 7C:
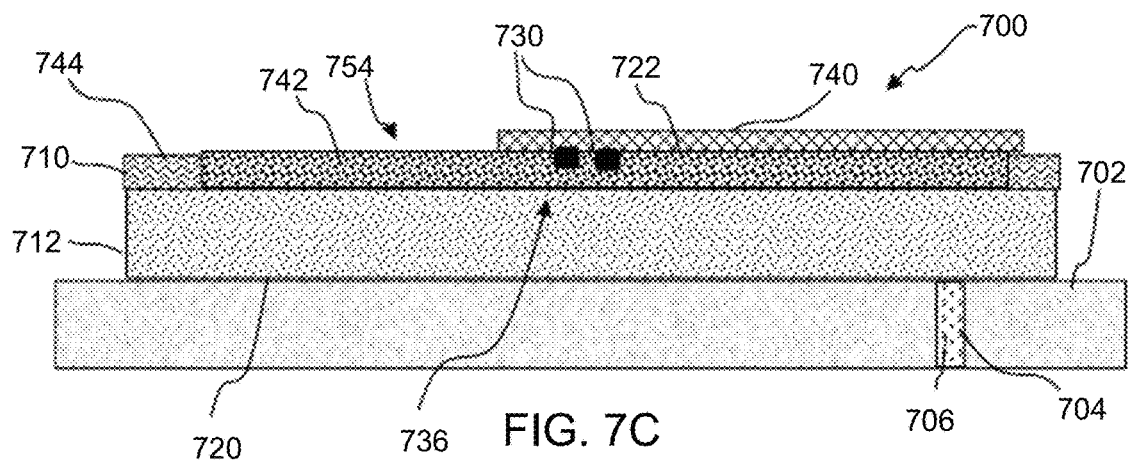
FIG. 7C is a cross-section view of the detector in FIG. 7A having a porous layer with two asymmetrical porous materials in accordance with embodiments disclosed herein.

FIG. 7C is a cross-sectional view of one embodiment of a detector 700 along line A-A and shows an addition of an open porous layer, e.g., first porous layer 712, between the fluid-collecting porous material (second porous layer) 710, and skin 702. The first porous layer 712 includes a sample-collection surface 720, and the second porous layer 710 includes an analyte detection surface 722. The sample is taken up through the first porous layer 712 and delivered to the collection zone of the second porous layer 710. As the sample flows in pathway 726 past the sensors 730 the various analytes may be detected. The evaporation zone of the second porous layer 710 allows replenishment of the sample through the first porous layer 712.

EXAMPLES

The following examples provide various non-limiting embodiments and properties of the present invention. Although certain methods and equipment are described below, other methods or equipment determined suitable by one of ordinary skill in the art may be alternatively utilized.

Thickness

Figure 15A:
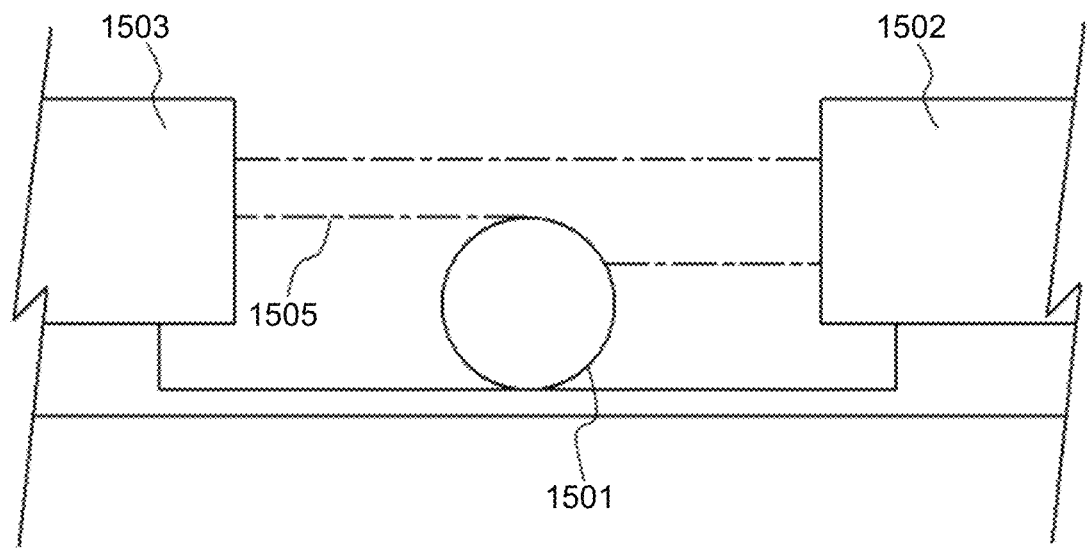
FIGS. 15A and 15B are schematics of the thickness measuring apparatus used to determine thickness of materials used in the Examples.
Figure 15B:
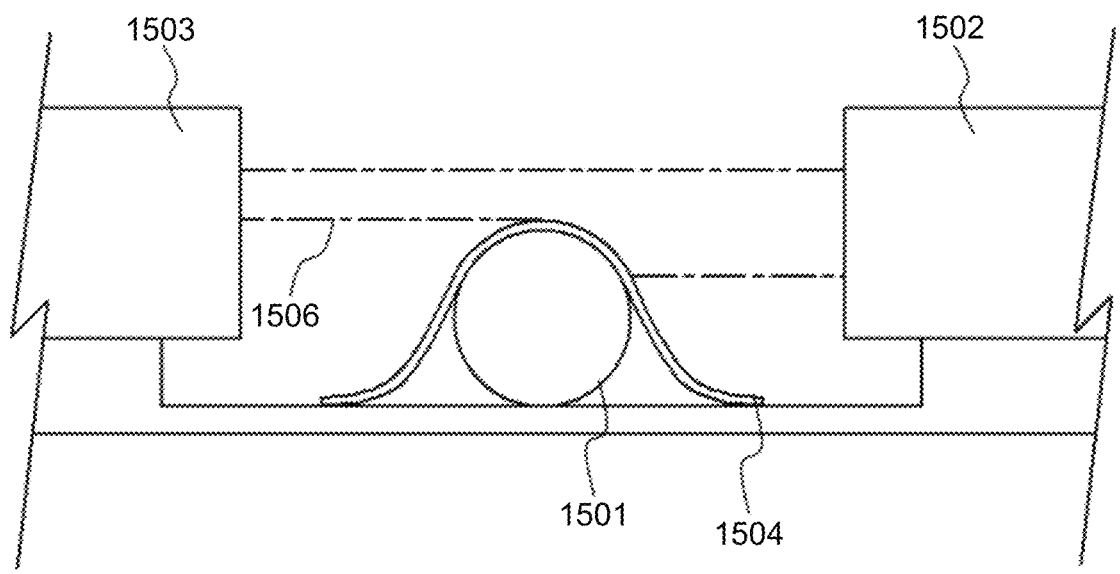

Thickness was measured using a laser micrometer (Keyence model no. LS-7010). As shown in FIGS. 15A and B, a metal cylinder 1501 was aligned between a laser micrometer source 1502 and a laser micrometer receiver 1503. The shadow 1505 of the top of the cylinder 1501 is projected onto receiver 1503 as shown in FIG. 15A. The position of the shadow was then reset as the "zero" reading of the laser micrometer. As shown in FIG. 15B, a single layer of membrane 1504 is draped over the surface of the metal cylinder 1501 without overlap and without wrinkles, casting shadow 1506 onto the receiver 1503. The laser micrometer then indicated the change in the position of the shadows 1505 and 1506 as the thickness of the sample. Each thickness was measured three times and averaged for each sample.

Gurley

The Gurley air flow test (Gurley Model 4340 Automatic Densometer) measures the time in seconds for 100 cm³ of air to flow through a 6.45 cm² sample at 12.4 cm of water pressure.

Matrix Tensile Strength (for Membranes)

Samples were prepared by using a die punch to cut ASTM D412 Type F dogbone samples out of the ePTFE membrane. The membrane was placed on the cutting table such that it was free from wrinkles in the area where the sample was to be cut. The die was then placed on the membrane (generally in the center 200 mm of the web) such that its long axis was parallel to the direction that would be tested. Once the die was aligned, pressure was applied to it to cut through the membrane web. Upon removal of this pressure, the dogbone sample for testing was inspected to ensure it was free from edge defects which may impact the tensile testing. At least 3 samples in the machine direction and three samples in the transverse direction were prepared in this manner. Once samples were prepared, they were measured to determine their mass using an analytical balance and their thickness using a Mitutoyo 547-400S thickness gage. Note that any suitable means for measuring thickness can be used. Each sample was subsequently tested to determine its tensile properties using an Instron 5500 tensile tester. The samples were inserted into the tensile tester and held using Instron Catalog 2702-015 (rubber coated face plate) and 2702-016 (serrated face plate) grip plates such that each end of the sample was held between one rubber coated and one serrated face plate. The pressure applied to the grip plates was approximately 552 kPa. The gauge length between the grips was set at 58.9 mm and the crosshead speed (pulling speed) was set to a speed of 508 mm/min. A 500 N load cell was used to carry out these measurements and data was collected at a rate of 50 points/sec. The laboratory temperature was between 20 and 22.2 degrees Celsius to ensure comparable results. Finally, if the sample happened to break at the grip interface, the data was discarded. At least 3 samples in the machine direction and three samples in the transverse direction were successfully pulled (no slipping out of or breaking at the grips) in order to characterize the membrane web.

The following equation was used to calculate the matrix tensile strength:

$$MTS = ((F_{max}/w)*p)/\text{mass:area}$$

in which: MTS=matrix tensile strength in MPa, $F_{max}$=maximum load measured during test (Newtons), w=width of dogbone sample within the gauge length (meters), p=density of PTFE ($2.2 \times 10^6$ g/m³), mass:area=mass per area of sample as described below (g/m²).

Bubble Point

Bubble point pressures were measured according to the general teachings of ASTM F31 6-03 using a Capillary Flow Porometer (Model 3 Gzh from Quantachrome Instruments, Boynton Beach, Fla.). The sample membrane was placed into the sample chamber and wet with Silwick Silicone Fluid (available from Porous Materials Inc.) having a surface tension of 20.1 dynes/cm. The bottom clamp of the sample chamber had a 2.54 cm diameter, 0.159 cm thick porous metal disc insert (Quantachrome part number 75461 stainless steel filter) was used to support the sample. Using the 3GWin software version 2.1 the following parameters were set as specified in the table immediately below. The values presented for bubble point pressure are the average of two measurements.

Bubble point pressure was converted to pore size using the following equation:

$$D_{BP} = 4\gamma^{lv} \cos \Theta / P_{BP}$$

where $D_{BP}$ is the pore size, $\gamma^{lv}$ is the liquid surface tension, $\Theta$ is the contact angle of the fluid on the material surface, and $P_{BP}$ is the bubble point pressure. It is understood by one skilled in the art that the fluid used in a bubble point measurement must wet the surface of the sample.

Mass to Area

The mass per area of samples was measured according to the ASTM D 3776 (Standard Test Methods for Mass Per Unit Area (Weight) of Fabric) test method (Option C) using a Mettler-Toledo Scale, Model 1060. The scale was recalibrated prior to weighing specimens, and the results were reported in grams per square meter (g/m$^2$).

Electrical Continuity Test

Figure 16:
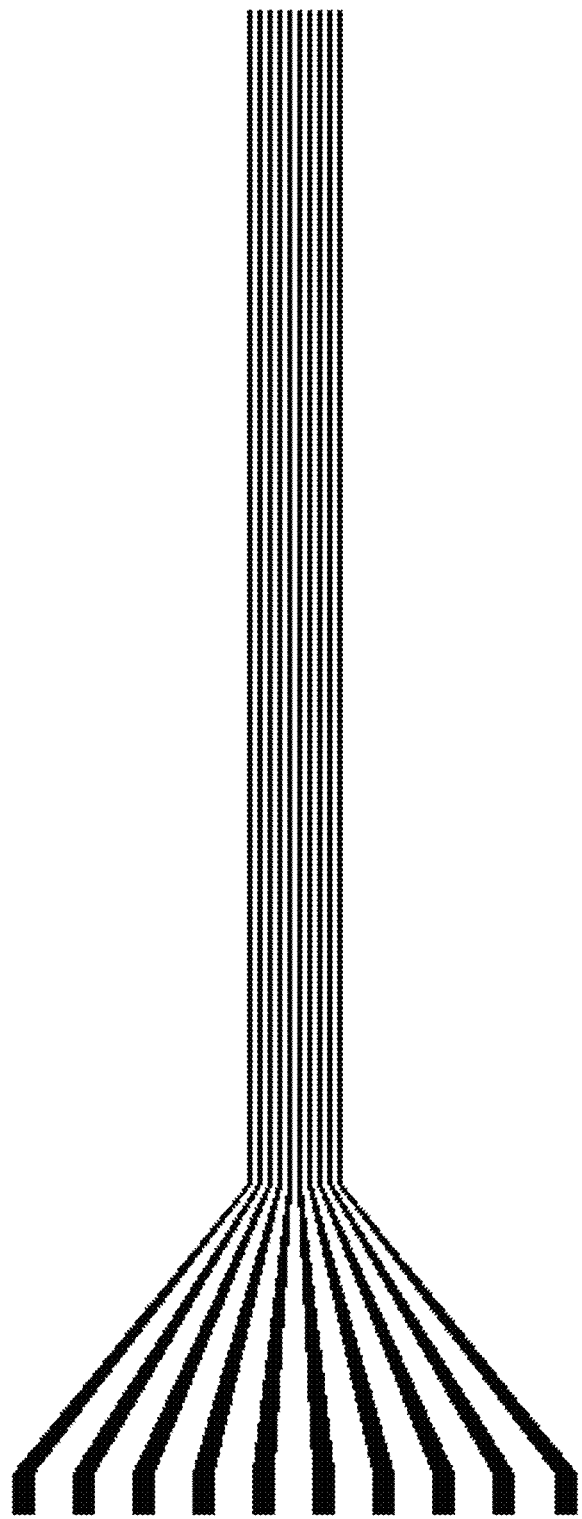
FIG. 16 is an illustration of a conductive ink pattern used in an electrical continuity test.

An electrical continuity sensor was fabricated in the following manner. A 50 micron thick PET film 8567K22 (McMaster Carr, Robbinsville, N.J.) was obtained. The PET film was screen-printed using conductive ink in the pattern shown in FIG. 16. The pattern consists of 10 parallel traces, each with a width of approximately 370 microns and spaced at a pitch of 1 mm. At one end of the parallel traces, the printed features increase in width and spacing and terminate in 2 mm wide pads. The conductive ink used was PE874 (E. I. du Pont de Nemours, Wilmington, Del.). The screen printing was performed using a model MSP-088 screen printer (HMI Manufacturing, Lebanon, N.J.), a stainless steel screen with 200 TPI (threads/wire per inch; ~78.74 wires per cm), 1.6 mil (~40.64 µm) wire diameter, and a 12.7 micron emulsion of the ink. After printing the ink was then dried in a convection oven at 120° C. for 10 minutes.

The continuity sensor was placed on a flat smooth surface with the printed surface facing up. A membrane being tested was placed on the surface of the continuity sensor.

A 100 nanoliter drop of saline solution 245-09-0072 (Target, Minneapolis, Minn.) was dispensed using a 0.5 microliter syringe 5190-0464 (Agilent, Santa Clara, Calif.) onto the simulated skin surface described in Comparative Example A. The simulated skin surface was placed face down on the membrane and continuity sensor so that the droplet of saline was approximately centered within the ten, parallel traces. A 200 gram weight was placed on top of the simulated skin to ensure good contact between the simulated skin, the membrane, and the continuity sensor, and a timer was started. A Fluke 116 multimeter (Fluke Corporation, Everett, Wash.) was used in autorange mode to measure the electrical resistance between the individual pairs of the 10 parallel traces by contacting the probe of the multimeter to the pad at the end of the selected trace. Continuity testing was first performed on the gap between adjacent parallel traces. Continuity is defined as having a resistance of 44 MOhms or less and demonstrates that the saline solution is in contact with both conductive traces being tested. If continuity was measured across a single gap, one probe was moved to the next pad and the continuity across 2 gaps was measured. This process was repeated until the largest number of gaps to measure continuity was identified. This number was recorded at 30 seconds, 2 minutes, and 5 minutes. The best performing continuity sensor is one that quickly spreads the fluid over the largest distance. One skilled in the art will recognize that any number of tests can be performed on the fluid once the fluid is delivered to the electrodes of the sensor.

Comparative Example A

Figure 8:
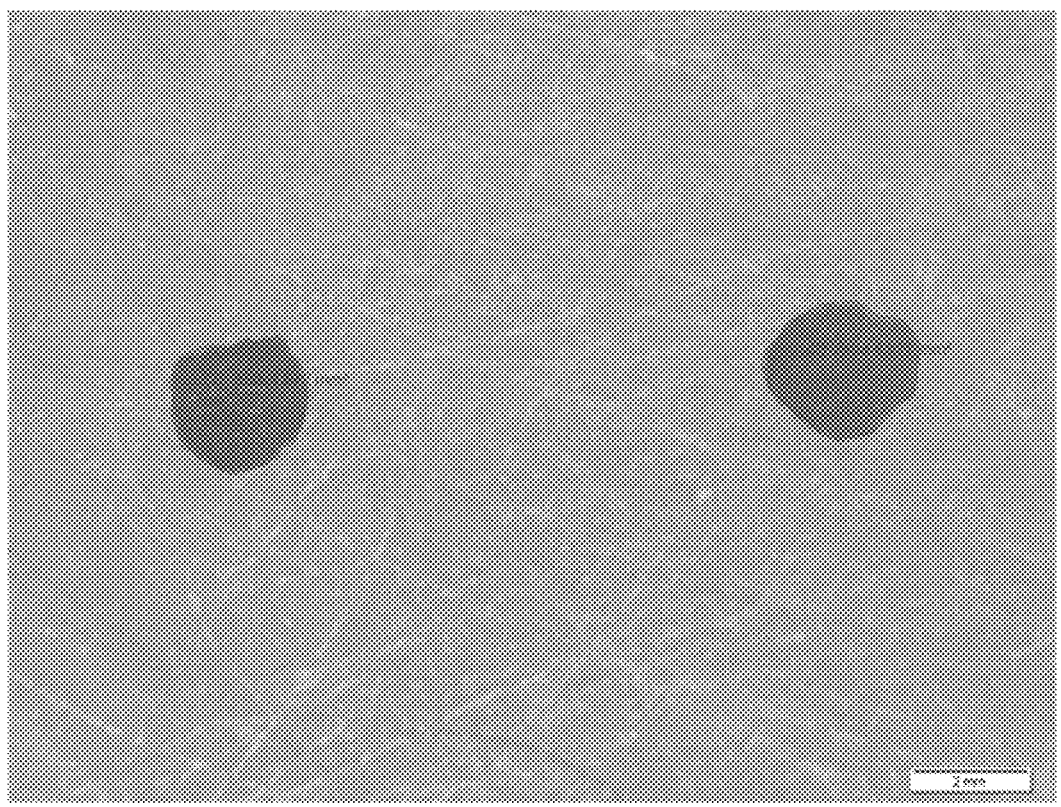
FIG. 8 is an image of the wetted area for Comparative Example A.
Figure 9A:
FIGS. 9A-9F are time-lapsed images of the wetted area for Example 1.
Figure 9B:
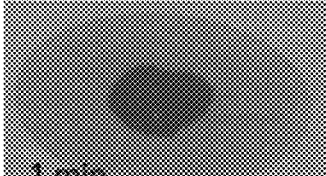
Figure 9C:
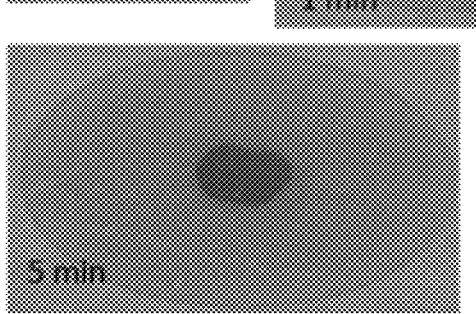
Figure 9D:
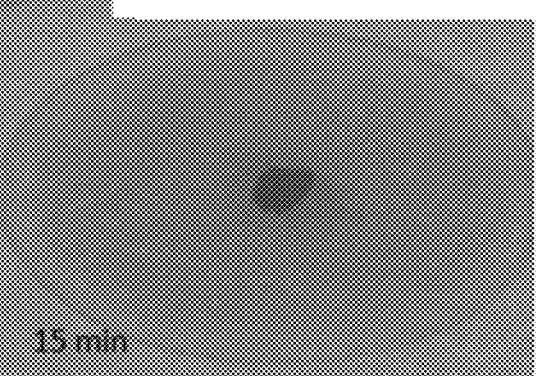
Figure 9E:
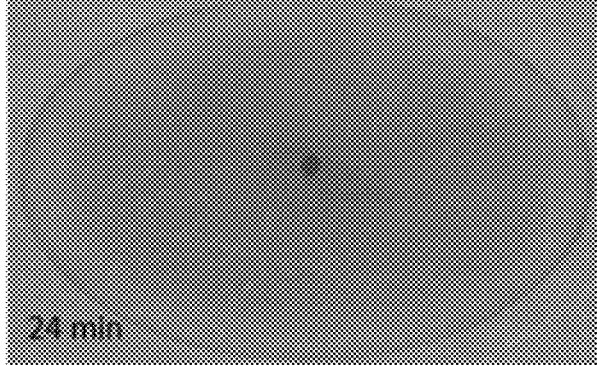
Figure 9F:
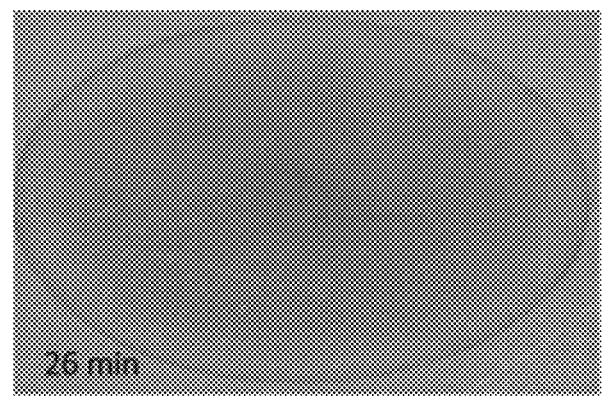

For Comparative Example A, a simulated skin surface was created by roughening up one face of a 6.35 mm thick sheet of polycarbonate with 80 grit sandpaper. 10 ml of water was colored blue by adding several drops of blue food coloring and mixing thoroughly. 250 nL of the blue water was deposited on the rough surface of the polycarbonate using a syringe. A glass cover slide was place on top of the water and the water was viewed from above using a light microscope. The water was allowed to spread out between the glass coverslip and the polycarbonate sheet, coming to rest after about a minute. The wetted area was approximately circular and measured to be 4.9 mm$^2$. Assuming a constant thickness, the 250 nL of water formed a 51 µm thick film between the simulated skin and the glass cover slip. FIG. 8 is an image of the wetted area of two drops of water on the simulated skin surface.

Comparative Example B

The Electrical Continuity Test was performed as described, except the membrane was excluded. In other words, the 100 nL water droplet dispensed on the simulated skin was placed directly onto the parallel traces of the electrical continuity sensor. The largest number of gaps to measure conductivity after 30 seconds was 1, after 2 minutes was 1 and after 5 minutes was 1.

Example 1

Figure 10:
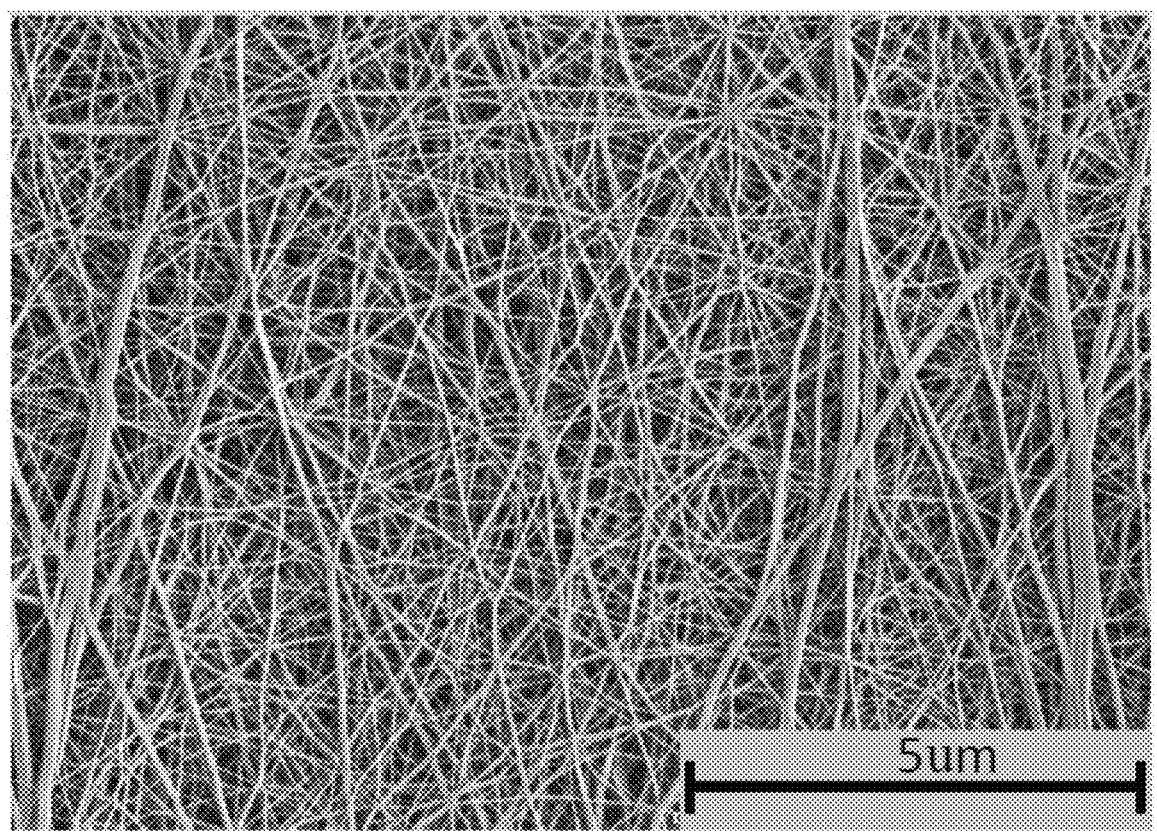
FIG. 10 is a SEM image of the porous material in Example 1.
Figure 11A:
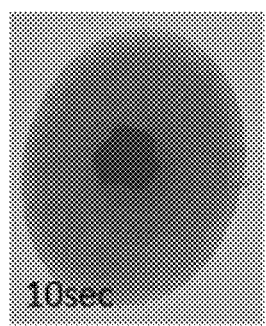
FIGS. 11A-11D are time-lapsed images of the wetted area for Example 2.
Figure 11B:
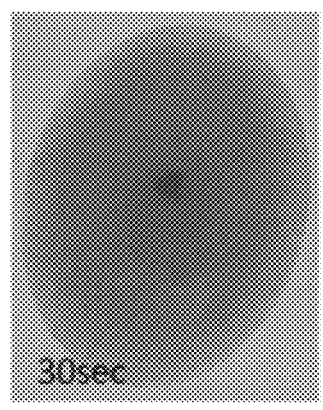
Figure 11C:
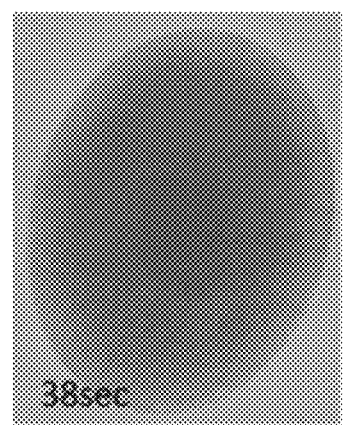
Figure 11D:
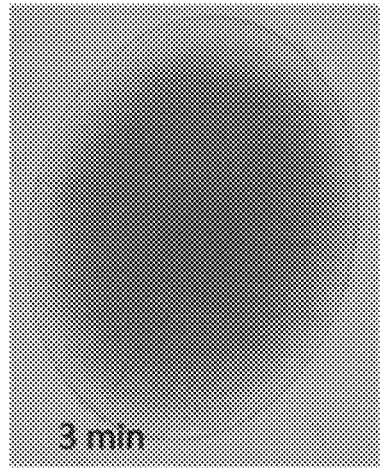

For Example 1, a porous expanded PTFE membrane was made based on the teachings of U.S. Pat. No. 7,306,729, with a mass/area of 0.69 g/m2, a thickness of 5.0 µm, a porosity of 93.8%, a bubble point of 505.3 KPa, a bubble point pore diameter of 0.144 µm, having a Gurley airflow of 1.26 sec, and matrix tensile properties of 771 MPa in the longitudinal direction and 345 MPa in the transverse direction. A scanning electron micrograph of the surface of the membrane can be seen in FIG. 10.

A coating solution was prepared by dissolving 3% Soarnol EVOH (Nippon Gohsei, Arlington Heights, Ill.) into a solvent blend comprising 2-butanol, isopropyl alcohol and deionized water in the ratios of 1:2:3.53 respectively. The mixture was heated to 80° C. for 4 hours with stirring, causing the polymer pellets to completely dissolve and create a clear solution. The solution was cooled to room temperature.

The ePTFE membrane was mounted in a 100 mm diameter embroidery hoop and the coating solution was applied to the ePTFE with a gloved finger, spreading it across the membrane. Excess solution was blotted away using a paper lab wipe. The coated membrane was placed in an oven at 80° C. for 5 minutes to dry off the solvent, resulting in a coating of EVOH on the node and fibril structure of the ePTFE. The thickness of the EVOH coated ePTFE was 1.76 µm.

The wetting characteristic of the membrane was tested by first placing a 250 nL drop of water as described in Comparative Example A onto the roughened side of the polycarbonate sheet described in Comparative Example A. A 30 mm square of the coated ePTFE membrane was cut from the sample and placed on top of a 22 mm square glass microscope coverslip, with the excess membrane wrapped around to the back of the coverslip. The coverslip and membrane were placed on top of the drop of water with the membrane side against the water. A timer was started and the water was viewed from above using a light microscope. The area of the wetted region was measured at various time intervals and can be seen in FIGS. 9A-9F. The presence of the ePTFE membrane resulted in a much larger wetted area against the coverslip than without the ePTFE membrane. If the coverslip were replaced with a sensor, a much greater surface area of the sensor would be able to interact with the fluid with the inclusion of the ePTFE membrane. Table 1 reports the wetted area v. time in minutes for Example 1.

TABLE 1

Example 1

| Time (min) | Area (mm²) |
| --- | --- |
| 0.167 | 13.388 |
| 0.5 | 19.753 |
| 1 | 26.76 |
| 2.333 | 39.607 |
| 3.333 | 47.87 |
| 4 | 52.435 |
| 5 | 58.468 |
| 7 | 69.772 |
| 9 | 76.492 |
| 12 | 88.039 |
| 15 | 95.903 |
| 18 | 101.174 |
| 21 | 105.942 |
| 24 | 109.252 |
| 25.767 | 109.996 |

Example 2

Figure 12:
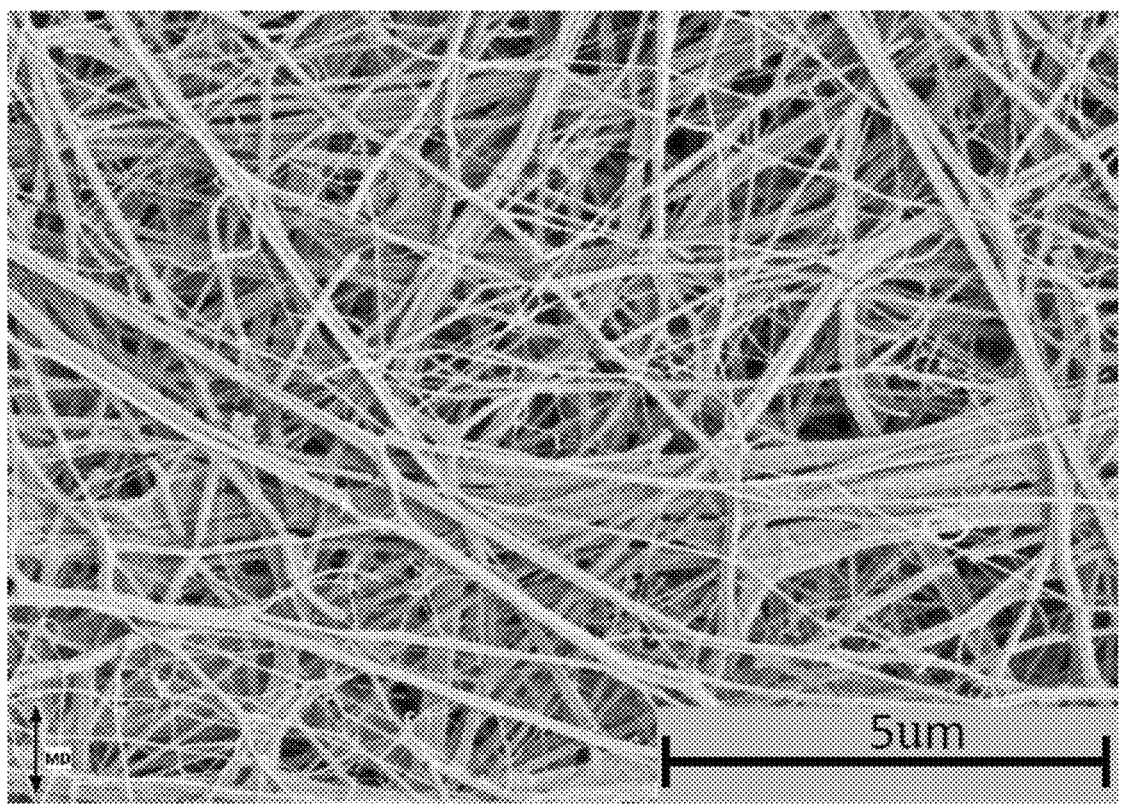
FIG. 12 is a SEM image of the porous material in Example 2.
Figure 13A:
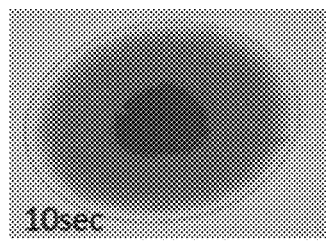
FIGS. 13A-13D are time-lapsed images of the wetted area for Example 3.
Figure 13B:
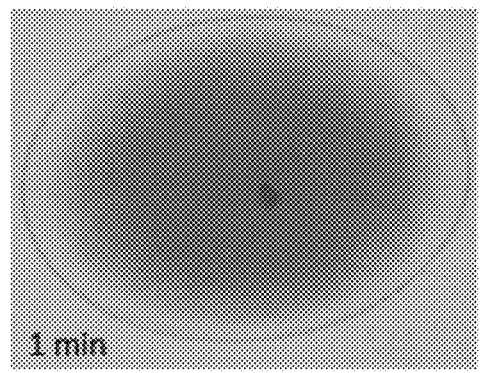
Figure 13C:
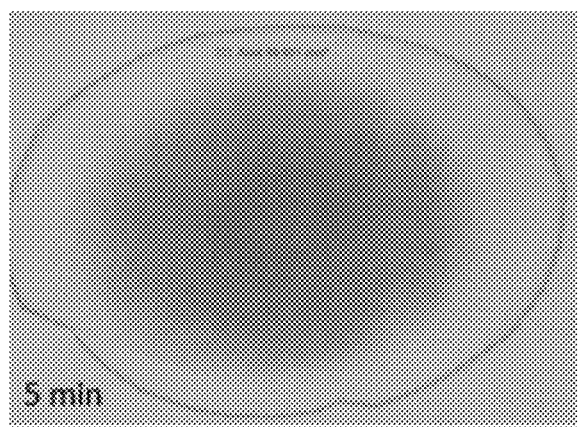
Figure 13D:
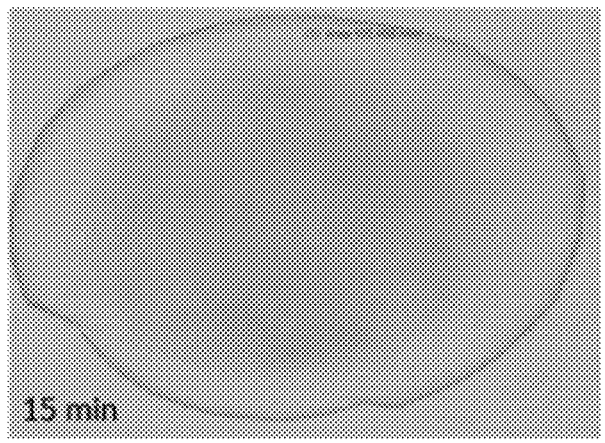

For Example 2, a porous expanded PTFE membrane was made based on the teachings of WO2004079208A3, with a mass/area of 4.1 g/m2, a thickness of 15.1 µm, a porosity of 87.9%, a bubble point of 187.25 kPa, a bubble point pore diameter of 0.3768 µm, having a Gurley airflow of 4.5 sec, and Matrix tensile properties of 258 MPa in the longitudinal direction and 328 MPa in the transverse direction. A scanning electron micrograph of the surface of the membrane can be seen in FIG. 12.

An EVOH coating solution was prepared as described in Example 1. The porous expanded PTFE was coated as described in Example 1. The thickness of the EVOH coated ePTFE was 10.3 µm.

The wetting characteristic of the membrane was tested by first placing a 250 nL drop of water as described in Comparative Example A onto the roughened side of the polycarbonate sheet described in Comparative Example A. A 30 mm square of the coated expanded PTFE membrane was cut from the sample and placed on top of a 22 mm square glass microscope coverslip, with the excess membrane wrapped around to the back of the coverslip. The coverslip and membrane were placed on top of the drop of water with the membrane side against the water. A timer was started and the water was viewed from above using a light microscope. The area of the wetted region was measured at various time intervals and can be seen in FIGS. 11A-11D.

The presence of the expanded PTFE membrane resulted in a much larger wetted area against the coverslip than without the expanded PTFE membrane. If the coverslip were replaced with a sensor, a much greater surface area of the sensor would be able to interact with the fluid with the use of the expanded PTFE membrane. In comparison to the performance of the membrane in Example 1, this embodiment results in a smaller wetted area, but a much faster wetting rate. Table 2 reports the wetted area v. time in minutes for Example 2.

TABLE 2

Example 2

| Time (min) | Area (mm²) |
| --- | --- |
| 0.167 | 32.094 |
| 0.5 | 54.066 |
| 0.633 | 60.953 |

TABLE 2-continued

Example 2

| Time (min) | Area (mm²) |
| --- | --- |
| 3 | 73.616 |
| 4 | 73.012 |

Example 3

A small pore ePTFE membrane as described in Example 1 and a large pore membrane as described in Example 2 were layered one on top of the other and mounted in a 100 mm diameter embroidery hoop.

An EVOH coating solution was prepared as described in Example 1. The coating solution was applied to the large pore ePTFE with a gloved finger, spreading it across the membrane. The coating solution wet through both the large and small pore membrane. Excess solution was blotted away using a paper lab wipe. The coated layered membrane was placed in an oven at 80° C. for 5 minutes to dry off the solvent, resulting in a coating of EVOH on the node and fibril structure of the ePTFE. The thickness of the EVOH coated layered ePTFE was 10.0 µm.

The wetting characteristic of the layered ePTFE was tested by first placing a 250 nL drop of water as described in Comparative Example A onto the roughened side of the polycarbonate sheet described in Comparative Example A. A 30 mm square of the coated layered ePTFE membrane was cut from the sample and placed on top of a 22 mm square glass microscope coverslip, with the excess membrane wrapped around to the back of the coverslip. The small pore membrane was positioned against the cover slip. The coverslip and layered membrane were placed on top of the drop of water with the large pore membrane side against the water. A timer was started and the water was viewed from above using a light microscope. The area of the wetted region was measured at various time intervals and can be seen in FIGS. 13A-13D. Table 3 reports the wetted area v. time in minutes for Example 3.

TABLE 3

Example 3

| Time (min) | Area (mm²) |
| --- | --- |
| 0.167 | 25.423 |
| 0.5 | 44.547 |
| 1 | 66.919 |
| 2 | 90.07 |
| 3.333 | 95.203 |
| 4.333 | 97.859 |
| 5 | 99.931 |
| 7 | 101.437 |
| 10 | 103.678 |
| 13 | 104.995 |
| 16 | 105.468 |
| 21 | 106.065 |

The presence of the layered ePTFE resulted in a much larger wetted area against the coverslip than without the ePTFE membrane. The layered membrane performed better than the large pore membrane described in Example 2 because the layered membrane created a much larger wetted area. The layered membrane performed better than the small pore membrane described in Example 1 because the layered membrane created a large wetted area much more quickly.

If the coverslip were replaced with a sensor, a much greater surface area of the sensor would be able to interact with the fluid with the inclusion of the layered ePTFE membrane as compared to the single layer ePTFE membrane, or without an ePTFE layer.

Figure 14:
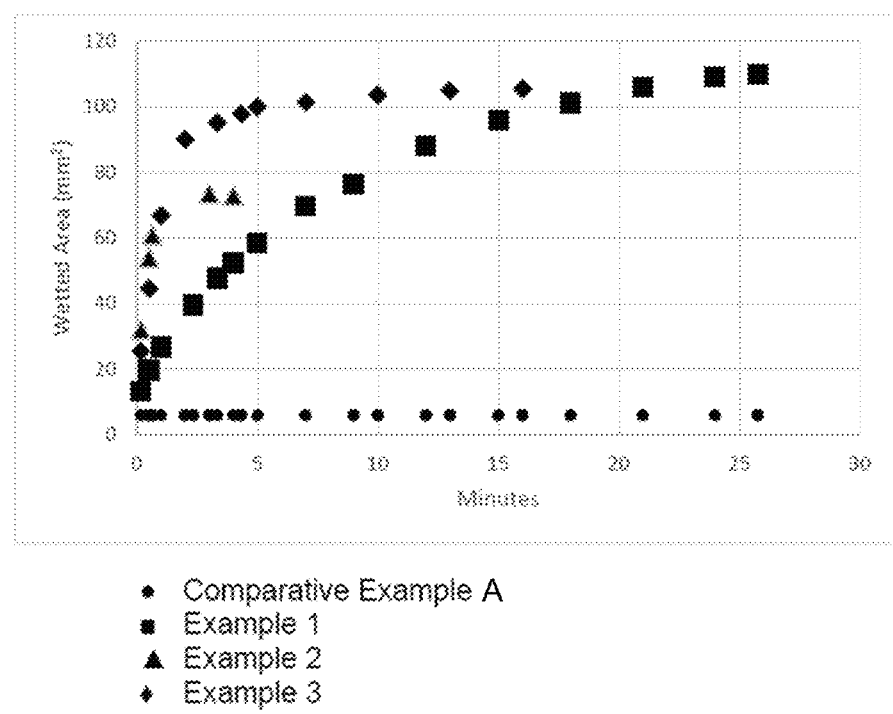
FIG. 14 is a graph comparing the wetted areas of the examples over time.

The results of Examples 1-3 are compared with Comparative Example A in the graph shown in FIG. 14. As shown, Comparative Example A fails to increase the wetted area, while Examples 1-3 show significant increases in the wetted area.

Example 4

The small pore ePTFE membrane described in Example 1 was mounted in a 100 mm diameter embroidery hoop and coated with the EVOH solution described in Example 1, using the method described in Example 1, resulting in a hydrophilic membrane. The thickness of the EVOH coated ePTFE was 2.1 µm.

The hydrophilic membrane was tested in the Electrical Continuity Test. The membrane was positioned on top of the continuity sensor so that the transverse direction of the membrane was parallel with the traces of the continuity sensor.

The largest number of gaps to measure conductivity after 30 seconds was 2, after 2 minutes was 4, and after 5 minutes was 6. This system is much more effective at spreading the fluid over a large distance as compared to the system without a hydrophilic membrane, as described in Comparative Example B.

Example 5

The large pore ePTFE membrane described in Example 2 was mounted in a 100 mm diameter embroidery hoop and coated with the EVOH solution described in Example 1, using the method described in Example 1, resulting in a hydrophilic membrane. The thickness of the EVOH coated ePTFE was 10.9 µm.

The hydrophilic membrane was tested in the Electrical Continuity Test. The membrane was positioned on top of the continuity sensor so that the longitudinal direction of the membrane was parallel with the traces of the continuity sensor.

The largest number of gaps to measure conductivity after 30 seconds was 5, after 2 minutes was 5, and after 5 minutes was 5. This membrane is much more effective at spreading the fluid over a large distance as compared to the system without a membrane, as described in Comparative Example B. This membrane was able to spread the fluid more quickly, but across a slightly shorter distance than the membrane described in Example 4.

Example 6

The small pore ePTFE membrane described in Example 1 and the large pore ePTFE membrane described in Example 2 were layered and coated as described in Example 3. The thickness of the layered EVOH coated ePTFE was 12.7 µm.

The hydrophilic layered membrane was tested in the Electrical Continuity Test. The membrane was positioned on top of the continuity sensor with the small pore ePTFE membrane in contact with the traces of the continuity sensor. The transverse direction of the small pore ePTFE was aligned the traces of the continuity sensor.

The largest number of gaps to measure conductivity after 30 seconds was 5, after 2 minutes was 7, and after 5 minutes was 7. This layered membrane is much more effective at spreading the fluid over a large distance as compared to the system without a membrane. This membrane was able to spread the fluid more quickly and across a larger distance than the membrane described in Example 4 and Example 5.

As used herein, the conjunction "and" is intended to be inclusive and the conjunction "or" is not intended to be exclusive unless otherwise indicated. For example, the phrase "or, alternatively" is intended to be exclusive.

The use of the terms "a", "an", "the", or similar referents in the context of describing the invention (especially in the context of the claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted.

As used herein, the term "about" refers to a degree of deviation typical for a particular property, composition, amount, value or parameter as identified; such as deviations based on experimental errors, measurement errors, approximation errors, calculation errors, standard deviations from a mean value, routine minor adjustments, and so forth.

As used herein, the term "conformable" is meant to describe a material structure that is extendable or extensible in a first direction, which recovers in a second direction perpendicular to the first direction, and which is elongated to take essentially the same shape as a non-planar substrate, e.g., human skin, without fracturing, tearing, or otherwise breaking.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed.

Detectors for detecting analytes have been described above both generically and with regard to specific embodiments. It will be apparent to those skilled in the art that various modifications and variations can be made in the embodiments without departing from the scope of the disclosure. Thus, it is intended that the embodiments cover modifications and variations provided they come within the scope of the appended claims and their equivalents.

What is claimed is:

1. A detector comprising:
    a first layer having a first side and a second side opposite the first side,
        wherein the first layer comprises a synthetic porous membrane having a first average pore size,
        wherein at least a portion of the first layer is hydrophilic, and
        wherein the first layer is configured to conform to the skin;
    a second layer having a first side and a second side opposite the first side,
        wherein the second layer is coupled to the first layer such that at least a portion of the first side of the second layer is directly adjacent to at least a portion of the second side of the first layer, wherein the second layer comprises a synthetic porous membrane having a second average pore size that is smaller than the first average pore size, and wherein at least a portion of the second layer is hydrophilic;

at least one sensor configured to detect an analyte in a sample collected on skin of a subject, wherein the at least one sensor is mounted to at least one of (a) the first layer, or (b) the second layer; and wherein the first layer includes a hydrophilic region and a hydrophobic region.

2. The detector of claim 1, further comprising a liquid-proof layer overlaying at least a portion of the second side of the second layer so as to cover the at least one sensor.

3. The detector of claim 1, wherein the second layer includes a hydrophilic region and a hydrophobic region.

4. The detector of claim 3, wherein the at least one sensor is mounted to the second side of the second layer so as to be positioned on the hydrophilic region of the second layer.

5. The detector of claim 3, wherein the hydrophobic region of the second layer comprises a barrier.

6. The detector of claim 3, wherein the hydrophobic region of the second layer comprises a barrier positioned on the second side of the second layer.

7. The detector of claim 6, wherein the at least one sensor is positioned between the barrier and the hydrophilic portion of the second layer.

8. The detector of claim 1, wherein a portion of the hydrophilic region of the first layer is offset from a portion of a hydrophilic region of the second layer.

9. The detector of claim 8, wherein the hydrophobic region of the first layer comprises a barrier positioned on the first side of the first layer.

10. The detector of claim 9, wherein the at least one sensor is positioned between the barrier and the hydrophilic portion of the first layer.

11. The detector of claim 1, wherein the at least one sensor is positioned between the hydrophilic region of the first layer and a hydrophilic region of the second layer.

12. The detector of claim 1, wherein at least one of (a) the first layer or (b) the second layer includes a fluoropolymer.

13. The detector of claim 12, wherein the fluoropolymer includes expanded polytetrafluoroethylene.

14. The detector of claim 1, wherein an average pore size of the first layer is from 0.04 to 200 µm.

15. The detector of claim 1, wherein an average pore size of the second layer is from 0.03 to 10 µm.

16. The detector of claim 1, wherein a bubble point of the first layer is from 0.3 to 1500 kPa.

17. The detector of claim 1, wherein a bubble point of the second layer is from 5 to 2000 kPa.

18. The detector of claim 1, wherein a bubble point of the second layer is from 1.1 to 1000 times greater than a bubble point of the first layer.

19. The detector of claim 1, wherein a bubble point of the second layer is from 1 to 1500 kPa greater than a bubble point of the first layer.

* * * * *